US009133567B2

(12) United States Patent
Seul

(10) Patent No.: US 9,133,567 B2
(45) Date of Patent: ***Sep. 15, 2015

(54) METHOD FOR DETERMINING AN ATTRIBUTE PROFILE OF BIOLOGICAL SAMPLES

(75) Inventor: Michael Seul, Basking Ridge, NJ (US)

(73) Assignee: Bioinventors & Entrepreneurs Network LLC, Warren, NJ (US)

( * ) Notice: Subject to any disclaimer, the term of this patent is extended or adjusted under 35 U.S.C. 154(b) by 365 days.

This patent is subject to a terminal disclaimer.

(21) Appl. No.: 13/190,154

(22) Filed: Jul. 25, 2011

(65) Prior Publication Data

US 2013/0029854 A1  Jan. 31, 2013

(51) Int. Cl.
| G01N 33/48 | (2006.01) |
| C40B 20/04 | (2006.01) |
| G01N 33/50 | (2006.01) |
| G01N 33/58 | (2006.01) |
| G01N 33/80 | (2006.01) |
| G06F 19/10 | (2011.01) |

(52) U.S. Cl.
CPC ................ C40B 20/04 (2013.01); G01N 33/50 (2013.01); G01N 33/582 (2013.01); G01N 33/80 (2013.01); G01N 2458/10 (2013.01); G06F 19/10 (2013.01)

(58) Field of Classification Search
CPC ....................................................... G06F 19/10
USPC .......................................................... 702/19
See application file for complete search history.

(56) References Cited

U.S. PATENT DOCUMENTS

| 5,144,139 | A | 9/1992 | Hillman et al. | |
|---|---|---|---|---|
| 6,114,179 | A | 9/2000 | Lapierre et al. | |
| 6,352,828 | B1 | 3/2002 | Brenner | |
| 7,081,339 | B2 | 7/2006 | Slepnev | |
| 7,083,914 | B2 | 8/2006 | Seul et al. | |
| 7,312,034 | B2 | 12/2007 | Virgos et al. | |
| 7,368,246 | B2 | 5/2008 | Slepnev et al. | |
| 7,387,887 | B2 | 6/2008 | Wittwer et al. | |
| 7,445,893 | B2 | 11/2008 | Slepnev | |
| 7,456,281 | B2 | 11/2008 | Dujols | |
| 7,498,054 | B2 | 3/2009 | Banerjee et al. | |
| 7,550,266 | B2 | 6/2009 | Slepnev | |
| 7,635,565 | B2 * | 12/2009 | Hashmi et al. ................ | 435/6.12 |
| 7,635,566 | B2 * | 12/2009 | Brenner ........................ | 435/6.18 |
| 7,858,307 | B2 | 12/2010 | Ho | |
| 7,871,770 | B2 | 1/2011 | Ho | |
| 8,021,842 | B2 * | 9/2011 | Brenner ........................ | 435/6.11 |
| 2005/0147998 | A1 | 7/2005 | White et al. | |
| 2006/0269932 | A1 | 11/2006 | Slepnev et al. | |
| 2007/0065864 | A1 | 3/2007 | Korzheva et al. | |
| 2007/0072223 | A1 | 3/2007 | Slepnev | |
| 2007/0077582 | A1 | 4/2007 | Slepnev | |
| 2009/0075274 | A1 | 3/2009 | Slepnev et al. | |
| 2009/0136951 | A1 | 5/2009 | Hart et al. | |

FOREIGN PATENT DOCUMENTS

WO    WO 0131056    3/2001

OTHER PUBLICATIONS

Hashmi et al., "A Flexible Array Format for Large-Scale, Rapid Blood Group DNA Typing", Transfusion, vol. 45, May 2005.*
'Blood Grouping Reagent Anti-D' product information, Micro Typing Systems Inc. [online], [retrieved on Apr. 11, 2011]. Retrieved from the California Blood Bank Society website using the Internet <URL: http://www.cbbsweb.org/enf/attachments/mts_dmonopi.pdf>.
Bosse, Yohan et al., "Identification of susceptibility genes for complex diseasesusing pooling-based genome-wide association scans," Jan. 29, 2009, Journal of Human Genetics, 125, pp. 305-318.
Cardoso et al, 1998 "Mini-pool screening by nucleic acid testing for hepatitis B virus, hepatitis C virus and HIV: preliminary results," Transfusion, 38(10): 905-907.
Chattopadhyay, P.K., et al., 2006, "Quantum dot semiconductor nanocrystals for immunophenotyping by polychromatic flow cytometry," Nat Med. 12(8): 972-7. Epub 2006, Jul. 23, Abstract only.
Colas, P., 2008, "The eleven-year switch of peptide aptamers," Journal of Biology, 7:2.
Crawford, M., et el 2003, "Peptide aptamers: Tools for biology and drug discovery," Briefings in Functional Genomics and Proteomics, 2 (1): 72-79.
Clavijio, O.P., et al., "HLA-Cw1701 is associated with two sub-Saharan African-derived HLA haplotypes: HLA-B*4201, DRB*03 and HLA-B*4202 without DRB1 *03," 1999, Tissue Antigens, 54, pp. 303-306.
Davis, J.A., et al., 2006, "Deterministic hydrodynamics: Taking blood apart," PNAS, 103(40):14779-14784.
Fawcett, T., 2006, "An introduction to ROC analysis," Pattern Recognition Letters 27: 861-874.
Farrar Kerrie et al., "Construction and screening of BAC libraries made from Brachypodium genomic DNA," Jun. 28, 2007, Nature Protocols, vol. 2 No. 7, pp. 1661-1674.
Gale, B.K. 'Bonding, Packaging and Sacrificial Processes' [online], 2001 [retrieved Apr. 11, 2011]. Retrieved from the Internet <URL: http://www.eng.utah.edu/~gale/mems/Lecture%2016a%20Bonding.pdf>.
Garcia, E.P., et al., 2005, "Scalable Transcriptional Analysis Routine-Multiplex Quantitative Real-Time Polymerase Chain Reaction Platform for Gene Expression Analysis and Molecular Diagnostics", Journal of Molecular Diagnostics, 7(4):444-454.

(Continued)

Primary Examiner — Jerry Lin
(74) Attorney, Agent, or Firm — Drinker Biddle & Reath LLP

(57) ABSTRACT

A method of identifying attributes in a plurality of biological samples including the steps of determining a source tag sharing number "d" for each of the attributes; providing a plurality of pools for the source tag sharing number "d" wherein each pool comprising a pooled subset of biological samples; for each pool of the plurality of pools, producing at least one pooled pool comprising attribute-specific reaction products comprising a marker tag that uniquely identifies an attribute and a source tag identifying said pool; and identifying said attribute-specific reaction products to identify the attributes. If "d" is equal to or larger than a maximum pool size, the reaction products may not comprise a source tag identifying each pool. Attributes may be binned together.

27 Claims, 27 Drawing Sheets

(56) References Cited

OTHER PUBLICATIONS

Herzenberg, L.A., et al., 2002, "The History and Future of the Fluorescence Activated Cell Sorter and Flow Cytometry: A View from Stanford," Clinical Chemistry 48(10); 1819-1827.

Iannone, Marie et al., "Multiplexed Single Nucleotide Polymorphism Genotyping by Oligonucleotide Ligation and Flow Cytometry," 2000, Cytometry, 39, pp. 131-140.

Kozlov, I.A., et al, 2004, "Efficient strategies for the conjugation of oligonucleotides to antibodies enabling highly sensitive protein detection," Biopolymers, 73(5): 621-30. Abstract only.

Lind and Kubista. Real-Time Immuno-PCR on the ICycler IQ™ System, Rev. A. [online], [retrieved on Apr. 4, 2011]. Retrieved from the Internet <URL: http://www.biocompare.com/Articles/ApplicationNote/1 173/Real-Time-Immuno-PCR-On-The-ICycler-IQ-System-Rev-A.html>.

Niemeyer, C.M., et al., 2005, "Immuno-PCR: high sensitivity detection of proteins by nucleic acid amplification," Trends in Biotechnology, 23(4): 208-216.

Pasanen, P.A., et al., 1993, "Receiver operating characteristic (ROC) curve analysis of the tumour markers CEA, CA 50 and CA 242 in pancreatic cancer; results from a prospective study," Br. J. Cancer (1993), 67: 852-855.

'Pooled BVD PCR Testing, Appendix I' Molecular Diagnostics [online], Jun. 30, 2011 [retrieved Jul. 13, 2011]. Retrieved from <URL: http://ahdc.vet.cornell.edu/docs/BVD_PCR_Pooled_Testing.pdf>.

Radisic, M., et al., 2006, "Micro- and nanotechnology in cell separation," International Journal of Nanomedicine: 1(1): 3-14.

Sacher et al., "Widmann's Clinical Interpretation of Laboratory Tests, 11th edition," F.A. Davis Company, Philadelphia, PA, 2000, chapter 1, pp. 3-7.

Sritharan, D. 'Size-based cell sorting by deterministic lateral displacement' Northeastern University, Chemical Engineering Master's Theses, Paper 8 [online], 2009 [retrieved Apr. 11, 2011]. Retrieved from the Internet <URL: http://hdl.handle.net/2047/d10019078>.

Stewart, C.C., et al., "Clinical Immunophenotyping by Flow Cytometry," Med TechNet Presentations [online], 1995 [retrieved Apr. 11, 2011]. Retrieved from the Internet <URL: http://www.medtechnet.com/public_pdf/mtc13.pdf>.

Taft Stevens, W., et al., 2008, "Introduction to BioArray Solutions' BeadChip Technology," Scientific Communications, ASHI Quarterly, Second Quarter [online], 2008 [retrieved Apr. 11, 2011]. Retrieved from the Internet <URL: http://www.immucor.com/bioarray/pdf/Introduction_to_BioArray_Solutions_BeadChip_Technology.pdf>.

Tyagi, Sanjay et al., "Molecular Beacons: Probes that Fluoresce upon Hybridization," Mar. 1996, Nature Biotechnology, 14, pp. 303-308.

'West Nile Virus-Procleix®WNV Assay—Summary Basis of Approval', Gen-Probe Incorporated [online], [retrieved on Apr. 11, 2011]. Retrieved from the US Food and Drug Administration using Internet <URL: http://www.fda.gov/downloads/BiologicsBloodVaccines/BloodBloodProducts/ApprovedProducts/LicensedProductsBLAs/BloodDonorScreening/InfectiousDisease/UCM090365.pdf>.

Won, J.I., et al., 2005, "Protein polymer drag-tags for DNA separations by end-labeled free-solution electrophoresis", Electrophoresis, 26: 2138-2148.

Zhao and Zhang, 2006, "Cellular mechanics study in cardiac myocytes using PDMS pillars array," Sensors and Actuators A: Physical, 125(2): 398-404.

Reischl, Udo, "PCR-Based Cloning and Subsequent Expression of Antigenic Proteins in *Escherichia coli*," Methods in Molecular Medicine, 1998, Molecular Diagnosis of Infectious Disease, 13, pp. 157-168.

Ye, Fei et al., "Fluorescent Microsphere-Based Readout Technology for Multiplexed Human Single Nucleotide Polymorhpism Analysis and Bacterial Identification," 2001, Human Mutation, 17, pp. 305-316,.

Vreeland, Wyatt. N. et al., "Multiplexed, High-Throughput Genotyping by Single-Base Extension and End-Labeled Fre-Solution Electrophoresis," Sep. 1, 2002, Analytical Chemistry, vol. 74, No. 17, pp. 4328-4333.

Office Action mailed Aug. 30, 2012; U.S. Appl. No. 13/190,147.
Office Action mailed Sep. 5, 2012; U.S. Appl. No. 13/190,163.
Office Action mailed Mar. 28, 2013, U.S. Appl. No. 13/190,147.
Office Action mailed May 30, 2013; U.S. Appl. No. 13/190,163.

* cited by examiner (c) for each pool of the plurality of pools for the source tag sharing number "d", produce at least one pooled pool comprising attribute-specific source-tagged reaction products from at least two pools of the plurality of pools for each of the different determined source tag sharing numbers "d", wherein the attribute-specific source tagged reaction products comprise a source tag identifying said each pool and a marker tag that uniquely identifies an attribute, by;

(i) performing a reaction in the pool to produce source-tagged reaction products comprising a source tag identifying said each pool;

(ii) pooling in at least one pooled pool at least some of the said produced source-tagged reaction products from at least two pools of the plurality of pools for the source tag sharing number "d", thereby providing a plurality of pooled pools comprising at least one pooled pool for each of the different determined source tag sharing numbers "d"

(iii) for each of the attribute to be identified, performing a second reaction using said source-tagged reaction products to produce attribute-specific source-tagged reaction products comprising a marker tag, wherein said marker tag uniquely identifies an attribute, and wherein said second reaction is in said pooled pool for the source tag sharing number "d", the "d" corresponding to the source tag sharing number "d" determined for the attribute in step (a)

(c) for each pool of the plurality of pools for the source tag sharing number "d", produce at least one pooled pool comprising attribute-specific source-tagged reaction products from at least two pools of the plurality of pools for each of the different determined source tag sharing numbers "d", wherein the attribute-specific source-tagged reaction products comprise a source tag identifying said each pool and a marker tag that uniquely identifies an attribute, by;
(i) performing a reaction in the pool to produce source-tagged reaction products comprising a source tag identifying said each pool;
(ii) for each of the alleles to be identified, performing a second reaction using said source-tagged reaction products to produce attribute-specific source-tagged reaction products comprising a marker tag, wherein said marker tag uniquely identifies an attribute,
(iii) pooling in at least one pooled pool at least some of the said attribute-specific source-tagged reaction products from at least two pools of the plurality of pools for the source tag sharing number "d", thereby providing a plurality of pooled pools comprising at least one pooled pool for each of the different determined source tag sharing numbers "d"

(c) for each pool of the plurality of pools for the source tag sharing number "d", produce at least one pooled pool comprising attribute-specific source-tagged reaction products from at least two pools of the plurality of pools for each of the different determined source tag sharing numbers "d", wherein the attribute-specific source-tagged reaction products comprise a source tag identifying said each pool and a marker tag that uniquely identifies an attribute, by;

(i) for each of the attributes to be identified, performing a reaction in the pool using said biological samples to produce attribute-specific reaction products comprising a marker tag, wherein said marker tag uniquely identifies an attribute, (ii) performing a second reaction in the pool using said attribute-specific reaction products to produce attribute-specific source-tagged reaction products comprising a source tag identifying said each pool;

(iii) pooling in at least one pooled pool at least some of the said attribute-specific source-tagged reaction products from at least two pools of the plurality of pools for the source tag sharing number "d", thereby providing a plurality of pooled pools comprising at least one pooled pool for each of the different determined source tag sharing numbers "d"

(c) for each pool of the plurality of pools for the source tag sharing number "d", produce at least one pooled pool comprising attribute-specific source-tagged reaction products from at least two pools of the plurality of pools for each of the different determined source tag sharing numbers "d", wherein the attribute-specific source-tagged reaction products comprise a source tag identifying said each pool and a marker tag that uniquely identifies an attribute, by:

(i) for each of the attributes to be identified, performing a reaction in the pool using said biological samples to produce attribute-specific source-tagged reaction products comprising a marker tag and a source tag, wherein said marker tag uniquely identifies an attribute and said source tag identifying said each pool, (ii) pooling in at least one pooled pool at least some of the said attribute-specific source-tagged reaction products from at least two pools of the plurality of pools for the source tag sharing number "d", thereby providing a plurality of pooled pools comprising at least one pooled pool for each of the different determined source tag sharing numbers "d"

FIG. 9
Source Tags
s-1Ab-c
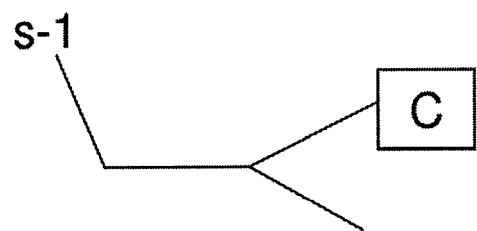
s-2Ab-c
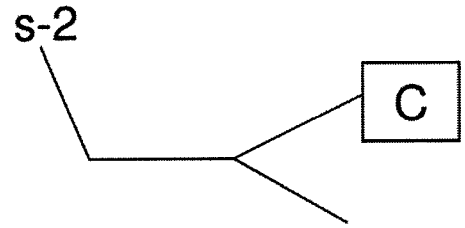
s-3Ab-c
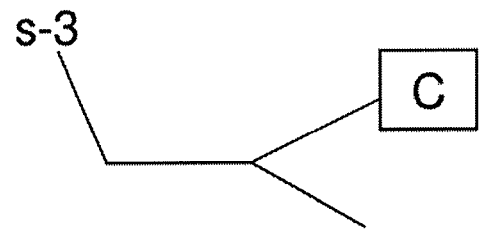

FIG. 14A

| Blood Group System | Antigens | Polymorphism |
|---|---|---|
| MNS | M \| N<br>S \| s | GYPA 59 C > T<br>GYPB 143 T > C |
| RhC | C \| c<br>V, VS | RHCE 307 C > T<br>733 C > G |
| RhE | E \| e | RHCE 676 G > C |
| Lutheran | Lu^a \| Lu^b | LU230 A > G |
| Kell | K \| k<br>Js(a)/Js(b)<br>Kp(a)/Kp(b) | KEL698 T > C<br>KEL1910 T > C<br>KEL961 T > C |
| Duffy | Fy^a \| Fy^b | FY125 G > A |
| Kidd | Jk^a \| Jk^b | JK838 G > A |
| Diego | Di^a \| Di^b | DI2561 T > C |
| Scianna | ScI \| ScII | SC169 G > A |
| Dombrock | Do^a \| Do^b<br>Hy \| Jo | DO323 G > T<br>DO350 C > T |
| Colton | Co^a, Co^b | CO134 C > T |
| Landsteiner-Wiener | LW^a, LW^b | LW308 A > G |

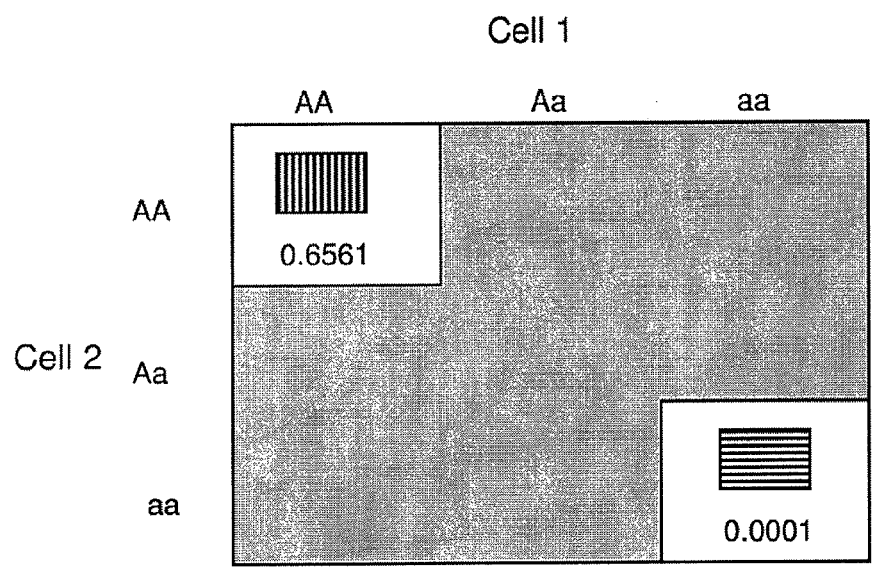

FIG. 17A

1700 — Caucasian

|  |  |  | 1768 MinFreq 0.001 | 1770 Cutoff (=C) 0.1800 | 1772 Max PoolSz 32 |  |  |
|---|---|---|---|---|---|---|---|

| 1750 Blood Grp System | 1752 ISBT Design | 1754 Alleles | 1756 A | 1758 B | 1760 f | 1762 d(s) | 1764 | 1766 pwr of 2 | 1774 32 | 16 | 8 | 4 | 2 | 1 |
|---|---|---|---|---|---|---|---|---|---|---|---|---|---|---|
| Kell | 6-KEL | K(1/2) | 0.03 | 0.97 |  | 3.2577 | 1 | 2 |  |  |  |  | K(1/2) |  |
| Lutheran | 5-LU | LU | 0.03 | 0.97 |  | 3.2577 | 1 | 2 |  |  |  |  | LU |  |
| MNSs | 2-MNS | GYPBS | 0.34 | 0.66 |  | 0.2388 | 0 | 1 |  |  |  |  |  | GYPBS |
| Dombrock | 14-DO | DO-793 | 0.37 | 0.63 |  | 0.2148 | 0 | 1 |  |  |  |  |  | DO-793 |
| Duffy | 8-FY | FY | 0.41 | 0.59 |  | 0.1881 | 0 | 1 |  |  |  |  |  | FY |
| Kidd | 9-JK | JK | 0.52 | 0.48 |  | 0.1517 | 0 | 1 |  |  |  |  |  | JK |
| MNSs | 2-MNS | GYPA | 0.57 | 0.43 | 0.43 | 0.1765 | 0 | 1 |  |  |  |  |  | GYPA |
| Duffy | 8-FY | GATA | 0.95 | 0.05 | 0.05 | 1.9345 | 3 | 8 |  |  |  |  |  | GATA |
| Duffy | 8-FY | FY265 | 0.99 | 0.01 | 0.01 | 9.8729 | 4 | 16 |  |  | FY265 |  |  |  |
| Scianna | 13-SC | SC(1/2) | 0.994 | 0.006 | 0.006 | 16.4879 | 5 | 32 |  | SC(1/2) |  |  |  |  |
| Hemoglobin S |  | HbS173 | 0.998 | 0.002 | 0.002 | 49.5631 | 6 | 32 | HbS173 |  |  |  |  |  |
| Colton | 15-CO | CO | 0.999 | 0.001 | 0.001 | 99.1758 | 6 | 32 | CO |  |  |  |  |  |
| Dombrock | 14-DO | DO-323 | 1 | 0 | 0.001 | 99.1758 | 6 | 32 | DO-323 |  |  |  |  |  |
| Dombrock | 14-DO | DO-350 | 1 | 0 | 0.001 | 99.1758 | 6 | 32 | DO-350 |  |  |  |  |  |
| Diego | 10-DI | DI (B/A) | 1 | 0 | 0.001 | 99.1758 | 6 | 32 | DI (B/A) |  |  |  |  |  |
| Landsteiner Wiener | 16-LW | LW | 1 | 0 | 0.001 | 99.1758 | 6 | 32 | LW |  |  |  |  | 1740 |
|  |  |  |  |  |  |  |  | 1730 | 6 |  1 | 1 | 0 | 2 | 6 |

Caucasian

| 1750 | 1752 | 1754 | 1756 | 1758 | 1760 | 1762 | 1764 | 1766 | 1774 | 16 | 8 | 4 | 2 | 1 |
|---|---|---|---|---|---|---|---|---|---|---|---|---|---|---|
| Blood Grp System | ISBT Design | Alleles | A | B | f | d(s) | | pwr of 2 | 32 | | | | | |
| Kell | 6-KEL | K(1/2) | 0.03 | 0.97 | | 3.2577 | 1 | 2 | | | | | K(1/2) | |
| Lutheran | 5-LU | LU | 0.03 | 0.97 | | 3.2577 | 1 | 2 | | | | | LU | |
| MNSs | 2-MNS | GYPBS | 0.34 | 0.66 | | 0.2388 | 0 | 1 | | | | | | GYPBS |
| Dombrock | 14-DO | DO-793 | 0.37 | 0.63 | | 0.2148 | 0 | 1 | | | | | | DO-793 |
| Duffy | 8-FY | FY | 0.41 | 0.59 | | 0.1881 | 0 | 1 | | | | | | FY |
| Kidd | 9-JK | JK | 0.52 | 0.48 | | 0.1517 | 0 | 1 | | | | | | JK |
| MNSs | 2-MNS | GYPA | 0.57 | 0.43 | 0.43 | 0.1765 | 0 | 1 | | | | | | GYPA |
| Duffy | 8-FY | GATA | 0.95 | 0.05 | 0.05 | 1.9345 | 3 | 8 | | | | | | GATA |
| Duffy | 8-FY | FY265 | 0.99 | 0.01 | 0.01 | 9.8729 | 4 | 16 | | | FY265 | | | |
| Scianna | 13-SC | SC(1/2) | 0.994 | 0.006 | 0.006 | 16.4879 | 5 | 32 | | SC(1/2) | | | | |
| Hemoglobin S | | HbS173 | 0.998 | 0.002 | 0.002 | 49.5631 | 6 | 32 | HbS173 | | | | | |
| Colton | 15-CO | CO | 0.999 | 0.001 | 0.001 | 99.1758 | 6 | 32 | CO | | | | | |
| Dombrock | 14-DO | DO-323 | 1 | 0 | 0.001 | 99.1758 | 6 | 32 | DO-323 | | | | | |
| Dombrock | 14-DO | DO-350 | 1 | 0 | 0.001 | 99.1758 | 6 | 32 | DO-350 | | | | | |
| Diego | 10-DI | DI (B/A) | 1 | 0 | 0.001 | 99.1758 | 6 | 32 | DI (B/A) | | | | | |
| Landsteiner Wiener | 16-LW | LW | 1 | | 0.001 | 99.1758 | 6 | 32 | LW | | | | | 1740 |
| | | | | | | | | 1730 | 6 | 1 | 1 | 0 | 2 | 6 |

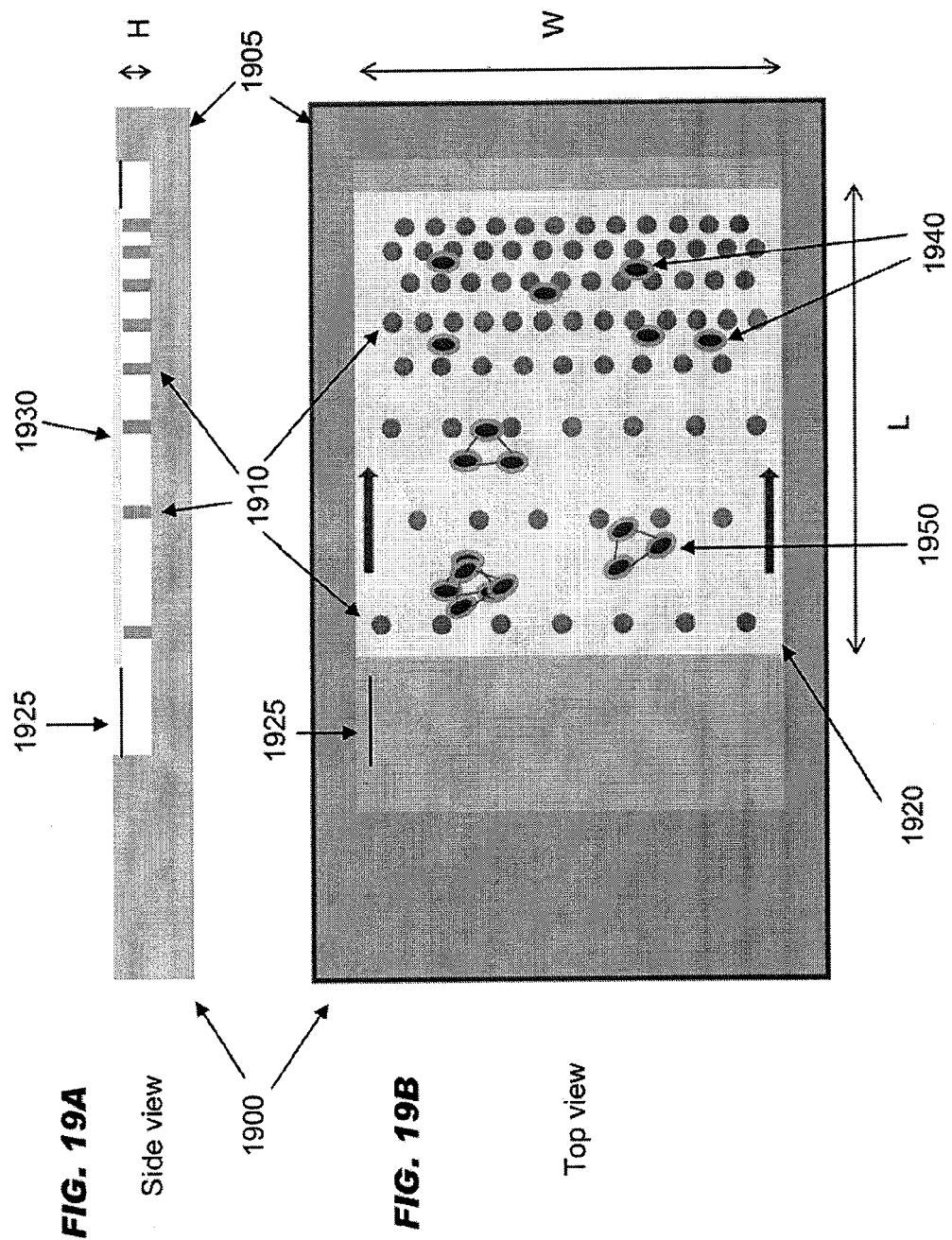
FIG. 19A Side view
FIG. 19B Top view

METHOD FOR DETERMINING AN ATTRIBUTE PROFILE OF BIOLOGICAL SAMPLES

FIELD

The invention relates to methods of determining an attribute profile for each of a plurality of biological samples, and more specifically to determining attribute profiles of biological samples by determining source tag sharing numbers for the alleles and by using source tags and marker tags where the source tags may be shared among different biological samples that have the same source tag sharing number.

BACKGROUND

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

In the field of medicine, it is increasingly desirable to stratify groups of individuals by molecular markers. Molecular markers for such stratification include sets of antigens, such as cell surface markers or blood cell antigens, and genetic variants of a set of genes. Identifying signatures of such molecular markers for a given disease or disorder can lead to prognostic and/or diagnostic methods. For instance, a set of 5 single nucleotide polymorphisms (SNPs) has been identified as having a significant association with prostate cancer (Zheng et al., 2008, N Engl J. Med. 358:910-919). Men having these 5 SNPs are at an increased risk of prostate cancer. Identifying signatures can also be useful for tissue matching. For instance, human leukocyte antigen (HLA) serotyping or genotyping can contribute to improved outcome for solid tissue or bone marrow transplantations (Sheldon and Poulton, 2006, Methods Mol Biol. 333: 157-174, 2006). Similarly, identifying blood cell antigens contributes to improved efficacy and reduced adverse clinical events for red blood cell transfusions. Thus, attribute profiling is of increasing interest and value in medicine.

In current practice, it is common to identify attribute profiles one sample at a time, and even one attribute at a time. Even with state-of-the-art methods of multiplex analysis, comprehensive attribute profiling of large numbers of individuals is time-consuming, laborious and thus, often impractical. A need exists for improved methods of attribute profiling.

SUMMARY

It is to be understood that both the foregoing general description and the following detailed description are exemplary and explanatory and are intended to provide further explanation of the invention.

A method of identifying attributes for at least two biological samples in a plurality of biological samples is disclosed. The method includes step (a) for each of the attributes to be identified, determining a source tag sharing number "d" for the attribute.

The method includes step (b) for each of the different determined source tag sharing numbers "d": (i) dividing the plurality of biological samples into sample subsets, each subset containing approximately the source tag sharing number "d" of biological samples so that each biological sample of the plurality of biological samples is included in at least one subset; and (ii) for each of the biological sample subsets, placing a portion of each of the biological samples included in the biological sample subset into a pool, thereby providing a plurality of pools for the source tag sharing number "d", wherein each pool comprises a pooled subset of biological samples.

The method includes step (c) for each pool of the plurality of pools for the source tag sharing number "d", producing at least one pooled pool comprising attribute-specific source-tagged reaction products from at least two pools of the plurality of pools for each of the different determined source tag sharing numbers "d", wherein the attribute-specific source-tagged reaction products comprise a source tag identifying said each pool and a marker tag that uniquely identifies an attribute.

The method includes step (d) identifying said attribute-specific source-tagged reaction products by interrogating said reaction products comprising said source tag and said marker tag, and if the interrogating of said reaction products indicate unambiguous results, then identifying said attributes, otherwise if the interrogating of said reaction products indicate ambiguous results, then disambiguating at least some of the ambiguous results, thereby identifying attributes for at least two biological sample in a plurality of biological samples.

Step (c) may comprise: for each pool of the plurality of pools for the source tag sharing number "d": (i) performing a reaction in the pool to produce source-tagged reaction products comprising a source tag identifying said each pool; (ii) pooling in at least one pooled pool at least some of the said produced source-tagged reaction products from at least two pools of the plurality of pools for the source tag sharing number "d", thereby providing a plurality of pooled pools comprising at least one pooled pool for each of the different determined source tag sharing numbers "d"; (iii) for each of the attributes to be identified, performing a second reaction using said source-tagged reaction products to produce attribute-specific source-tagged reaction products comprising a marker tag, wherein said marker tag uniquely identifies an attribute, and wherein said second reaction is in said pooled pool for the source tag sharing number "d", the "d" corresponding to the source tag sharing number "d" determined for the attribute in step (a).

Disambiguating the ambiguous results may include repeating the method of identifying attributes, wherein the attributes to be identified are each attribute that was not identified because the interrogating of said reaction products indicates said ambiguous results, wherein the plurality of biological samples comprise biological samples that comprise attributes that were not identified, and wherein step (a) may further include determining a lower source tag sharing number "d" than the previously determined source tag sharing number "d" for each attribute that cannot be identified because the interrogating of said reaction products indicates said ambiguous results. The attributes to be identified may further include other attributes not yet identified.

The source tag sharing number "d" for each attribute may be determined based on a frequency of an allele encoding said attribute.

In step (d) disambiguating the ambiguous results may include performing a method of deconvolution for each attribute that was not identified because the interrogating of said products indicates said ambiguous results.

The marker tag may comprise at least one of the following to identify an attribute: an oligonucleotide tag or a fluorescent tag.

Step (d) interrogating may include interrogating said source tag and said marker tag of said reaction products by contacting said reaction products with microparticles, said microparticles comprising a first capture probe complementary to said source tag and comprising an optical tag that identifies said microparticle. The microparticles may further include a second capture probe complementary to said marker tag, and wherein said marker tag is an oligonucleotide tag. The marker tag may include an optical tag. The optical tag may be a fluorescent tag.

In another embodiment, step (d) interrogating may include interrogating said marker tag of said reaction products by contacting said reaction products with anti-tags of said marker tags, and wherein said marker tag is an oligonucleotide tag; and identifying anti-tags that anneal to said oligonucleotide tags. Interrogating may include determining a length of the anti-tags by electrophoretic separation of said anti-tags. The anti-tags may further comprise an optical tag.

The source tag may include an unique nucleotide sequence.

The marker tag may include an unique nucleotide sequence.

The method may further include, prior to step (c)(iii), binning said attributes to be identified into one or more bins based on a frequency of said attributes; wherein in step (c)(iii) the second reaction is performed in a same pooled pool of said at least one pooled pool for each of the attributes grouped into a same bin of the plurality of bins, wherein two attributes are binned into the same bin only if the two attributes have the same source tag sharing number "d".

In an aspect, the attributes are antigens.

In an embodiment, each of the attributes identified may be an antigen of a blood group and attributes of a plurality of blood groups are identified and the marker tag uniquely identifies an antigen of a blood group.

In another aspect, the attributes identified may include expression levels of antigens in a collection of antigens, wherein altered expression levels of the antigens in said collection of antigens is associated with a medical condition.

In another aspect, the attributes identified may include the presence or absence of antigens in a collection of antigens.

The method may include, prior to step (c), adding to each pool of the plurality of pools an antibody specific to at least one attribute in each pool of the plurality of pools; contacting each pool with an agglutination agent; and assessing agglutination for each pool of the plurality of pools, wherein detecting the presence of agglutination indicates at least one biological sample of the pooled subset of biological samples comprises said at least one attribute.

The method may comprise identifying attributes wherein each of the attributes is an antigen of a blood group and attributes of a plurality of blood groups are identified. The marker tag may include an oligonucleotide tag comprising a first nucleotide sequence to identify an attribute and a second nucleotide sequence to identify a blood group. The marker tag may include an oligonucleotide that includes a nucleotide sequence to identify both a blood group system of the plurality of blood groups and said antigen.

In the method of identifying attributes wherein each of the attributes is an antigen of a blood group and attributes of a plurality of blood groups are identified, the marker tag of said reaction products may include at least one of the following to identify a blood group system of the plurality of blood groups: an oligonucleotide tag or a fluorescent tag.

Step (d) identifying said attributes of the plurality of blood groups may further include if said interrogating of said reaction products indicates attribute-specific reaction products in the same pooled pool with different marker tags for said blood group and "d"=1, then identifying a biological sample of the plurality of biological samples corresponding to a pool identified by said source tag as expressing both antigens of the blood group.

Step (d) identifying said attributes of the plurality of blood groups may further include if said interrogating of said reaction products indicates reaction products with marker tags that are the same in the same pooled pool for said blood group and "d">1, then identifying each of the biological samples used to form the pool identified by "d" as having the attribute identified by the marker tag.

A method of identifying attributes for at least two biological samples in a plurality of biological samples is disclosed. The method includes step (a) for each of the attributes to be identified, determining a source tag sharing number "d" for the attributes, wherein the source tag sharing number "d" for at least one of the attributes is equal to the maximum_pool_size.

The method includes step (b) for each of the different determined source tag sharing numbers "d": (i) dividing the plurality of biological samples into sample subsets, each subset containing approximately the source tag sharing number "d" of biological samples so that each biological sample of the plurality of biological samples is included in at least one subset; and (ii) for each of the biological sample subsets, placing a portion of each of the biological samples included in the biological sample subset into a pool, thereby providing a plurality of pools for the source tag sharing number "d", wherein each pool comprises a pooled subset of biological samples.

The method includes step (c) for each pool of the plurality of pools for the source tag sharing number "d," produce at least one pooled pool comprising attribute-specific reaction products: (i) for each pool of the plurality of pools for the source tag sharing number "d" where the source tag sharing number "d" is less than a maximum_pool_size, producing at least one pooled pool comprising attribute-specific source-tagged reaction products from at least two pools of the plurality of pools for each of the different determined source tag sharing numbers "d", wherein the attribute-specific reaction products comprise attribute-specific source-tagged reaction products comprising a source tag identifying said each pool and a marker tag that uniquely identifies an attribute; and (ii) for each pool of the plurality of pools for the source tag sharing number "d," where the source tag sharing number "d" is equal to the maximum_pool_size, producing at least one reaction pool comprising attribute-specific reaction products from each pool of the plurality of pools, wherein the attribute-specific reaction products comprise attribute-specific reaction products comprising biological samples comprising a marker tag that uniquely identifies an attribute, and wherein each said reaction pool is the at least one pooled pool.

The method includes step (d) identifying said reaction products comprising attribute-specific source-tagged reaction products or attribute-specific reaction products by interrogating said reaction products comprising said source tag and said marker tag, and if the interrogating of said reaction products indicates unambiguous results, then identifying said attributes, otherwise if the interrogating of said reaction products indicates ambiguous results, then disambiguating at least some of the ambiguous results, thereby identifying attributes for at least two biological samples in the plurality of biological samples.

In an embodiment, step (c)(i) may include for each pool of the plurality of pools for the source tag sharing number "d" where the source tag sharing number "d" is less than the maximum_pool_size: (i)(a) performing a reaction in the pool to produce source-tagged reaction products comprising a source tag identifying said each pool; (i)(b) pooling in at least one pooled pool at least some of the said produced source-tagged reaction products from at least two pools of the plurality of pools for the source tag sharing number "d", thereby providing a plurality of pooled pools comprising at least one pooled pool for each of the different determined source tag sharing numbers "d"; and (i)(c) for each of the attributes to be identified, performing a second reaction using said source-tagged reaction products to produce attribute-specific source-tagged reaction products comprising a marker tag, wherein said marker tag uniquely identifies an attribute, and wherein said second reaction is in said pooled pool for the source tag sharing number "d", the "d" corresponding to the source tag sharing number "d" determined for the attribute in step (a).

The maximum_pool_size may be a number of biological samples, wherein the number is based on technical limitations of performing the steps of the method.

The method of identifying attributes may include prior to step (c): binning said attributes to be identified into one or more bins based on a frequency of said attributes; wherein in step (c) producing at least one pooled pool comprising attribute-specific reaction products is performed in a same pooled pool of said at least one pooled pool for each of the attributes grouped into a same bin of the plurality of bins, wherein two attributes are binned into the same bin only if the two attributes have the same source tag sharing number "d."

Disambiguating the ambiguous results may include repeating the method of identifying attributes, wherein the attributes to be identified are each attribute that was not identified because the interrogating of said reaction products indicates said ambiguous results, wherein the plurality of biological samples comprise biological samples that comprise attributes that were not identified, and wherein step (a) may further include determining a lower source tag sharing number "d" than the previously determined source tag sharing number "d" for each attribute that cannot be identified because the interrogating of said reaction products indicates said ambiguous results. The attributes to be identified may further include other attributes not yet identified.

The method may include, prior to step (c), adding to each pool of the plurality of pools an antibody specific to at least one attribute in each pool of the plurality of pools; contacting each pool with an agglutination agent; and assessing agglutination for each pool of the plurality of pools, wherein detecting the presence of agglutination indicates at least one biological sample of the pooled subset of biological samples comprises said at least one attribute.

BRIEF DESCRIPTION OF THE DRAWINGS

The following detailed description can be read in connection with the accompanying drawings in which like numerals designate like elements and in which:

FIG. 4 schematically illustrates one embodiment of step 210 of FIG. 3, step 210.1;

FIG. 5 schematically illustrates another embodiment of step 210 of FIG. 3, step 210.2;

FIG. 6 schematically illustrates another embodiment of step 210 of FIG. 3, 210.3;

FIG. 7 schematically illustrates another embodiment of step 210 of FIG. 3, step 210.4;

FIG. 9 schematically illustrates source tags comprising a source tag such as "s-1" bound to a specific binding member "Ab-c";

FIG. 14A depicts a table of seventeen exemplary blood groups and the antithetical antigens for each group;

FIG. 16A schematically illustrates the visual labels that would be present for combinations of Cell-1 and Cell-2 having different phenotypes;

FIG. 16B schematically illustrates the probabilities of unambiguous results and ambiguous results for combinations of Cell-1 and Cell-2 having different phenotypes;

FIG. 17A schematically illustrates an example of determining the number "d" for a set of blood antigen groups with two sets of antigen frequencies, one for an African American population (first panel) and the other for a Caucasian population (second panel);

FIG. 19A schematically illustrates a side view of a device useful for assessing agglutination;

FIG. 19B schematically illustrates a top view of the device useful for assessing agglutination.

DETAILED DESCRIPTION

Definitions

Figure 1:
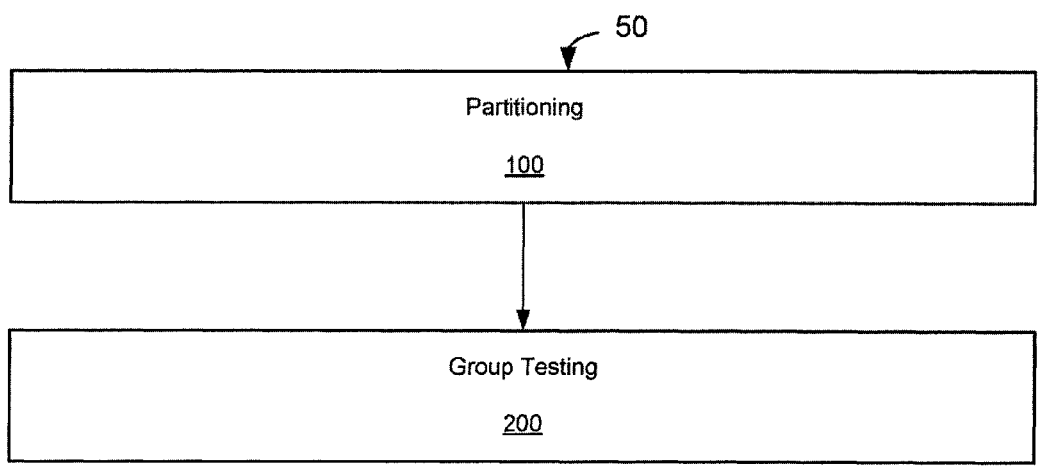
FIG. 1 schematically illustrates the method of determining an attribute profile for a plurality of biological samples.

Unless otherwise defined, all technical and scientific terms used herein have the same meaning as commonly understood by one of ordinary skill in the art to which this invention belongs. Still, certain elements are defined for the sake of clarity and ease of reference.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

A "biological sample" refers to biological material isolated or obtained from a living source. The material may contain any biological material suitable for detection, and may comprise or consist of cellular, sub-cellular and/or non-cellular material obtained from the individual. Exemplary biological samples include, but are not limited to, red blood cells, white blood cells, and platelets.

A "sub-cellular material" refers to a material that can be found in an intact cell in an organism but is present in a biological sample in the form of a non-intact cell, such as a fragment of a cell membrane or a collection of one or more types of organelles. Sub-cellular material may also comprise nucleic acid, such as DNA, mRNA, tRNA, siRNA, miRNA, and/or other transcription products present in a cell.

An "attribute" is a characteristic of a sample. Non-limiting examples of attributes include an antigen and a gene allele. Attribute characterization can include identifying the presence of one or more of a set of antigens (such as blood antigens), identifying the presence or absence of a specific antigen, identifying the relative amount of an antigen, and identifying a specific gene allele.

The phrase "identifying attributes for at least two biological samples" as used herein refers to assessing characteristics for at least two biological samples in a plurality of biological samples; for instance, identifying a first biological sample as having attributes $Lu^a$, ScI and $Co^a$ and identifying a second biological sample as having attributes $Lu^a$, ScI and $Co^a$. The phrase therefore encompasses both identifying the presence of a specific attribute, for instance, in a pool of biological samples, and identifying which biological sample or samples have that specific attribute. "To identify an attribute of a biological sample" and "to determine an attribute of a biological sample" are used interchangeably.

An "antigen," as used herein refers to any molecule to which a specific binding member can be prepared. Antigens include polypeptides, lipids, carbohydrates and combinations thereof such as glycoproteins and glycolipids. Non-limiting examples of antigens include blood cell antigens and human leukocyte antigens (HLA).

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants," "polymorphisms," or "mutations."

As used herein, "antithetical antigens" refers to the products encoded by allelic genes. Blood cell antigens are exemplary antithetical antigens.

An "attribute-specific probe" is a probe that binds preferentially to a target nucleotide sequence comprising a certain attribute. For instance, an "allele-specific probe" is a probe that binds preferentially to a target nucleotide sequence comprising a certain allele at a polymorphic site in comparison to other alleles of the same polymorphism.

An "allele-specific primer" is a primer that binds preferentially to a target nucleotide sequence comprising a certain allele at a polymorphic site and provides for amplification of the allele in comparison to other alleles of the same polymorphism; elongation of an allele-specific primer produces a product complementary to the template sequence so that, if template sequences differ, in positions other than that targeted by the primer, so will the sequences of the elongation products, and in such a case, an allele-specific primer also may be referred to as a "group-specific primer", the group comprising all alleles sharing the allele of the polymorphic site to which the primer is directed.

"Polypeptide" refers to a polymer composed of amino acid residues linked via peptide bonds. Polypeptides can be modified, such as glycoproteins, which are polypeptides that contain oligosaccharide chains covalently attached to polypeptide side-chains. Conventional notation is used herein to portray polypeptide sequences: the left-hand end of a polypeptide sequence is the amino-terminus; the right-hand end of a polypeptide sequence is the carboxyl-terminus.

The term "protein" typically refers to large polypeptides, i.e. polypeptides having greater than about 50 amino acids. The term protein can also encompass structures comprising two or more polypeptide chains in association, such as glycophorin A or T-cell receptor (TCR).

The term "peptide" typically refers to short polypeptides, i.e., polypeptides having between about 2 and about 50 amino acids.

As used herein, the term "specific binding member" refers to a member of a specific binding pair, i.e., two different moieties where one of the moieties through chemical or physical means specifically binds to the second moiety. A specific binding pair may be referred to as a specific binding member and its cognate binding partner. A moiety may be an individual molecule, such as a polypeptide, or may be two or more molecules, such as dimeric polypeptide structure. The term "binding pairs" or "binding partners" refers to two cognate compounds or molecules which specifically interact with each other. A non-limiting example of a specific binding member is an antibody. Another non-limiting example is an aptamer.

An "aptamer" refers to a oligonucleic acid molecule or peptide molecule that binds with high affinity and specificity to a target molecule.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and $F(ab)_2$, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody," as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

"Immunophenotyping" refers to the identification or characterization of cells using antibodies to antigens expressed by the cells.

The term "complementary" refers to nucleic acid sequences comprising complementary base-pairs according to the standard Watson-Crick base-pairing, or that are capable of hybridizing to a particular nucleic acid segment under relatively stringent conditions.

The term "gene" refers to a nucleic acid (e.g., DNA) sequence that comprises coding sequences necessary for the production of a polypeptide, precursor, or RNA (e.g., rRNA, tRNA). The term "gene" encompasses both cDNA and genomic forms of a gene.

The term "gene transcript" refers to a nucleic acid molecule that comprises the coding sequence for a specific polypeptide, precursor or RNA. Messenger RNA (mRNA) is an exemplary gene transcript. The term "gene transcript" encompasses cDNA forms of gene transcripts.

The term "hybridization" refers to the process in which two single-stranded nucleic acids bind non-covalently to form a double-stranded nucleic acid; triple-stranded hybridization is also possible under certain conditions. Complementary sequences in the nucleic acids pair with each other to form a double helix. The resulting double-stranded nucleic acid is a "hybrid." Hybridization may be between, for example two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support, such as a microparticle or a substrate for a nucleic acid array. Hybridization techniques may be used to detect and isolate specific sequences, measure homology, or define other characteristics of one or both strands.

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

"Ligation" means to form a covalent bond or linkage between the termini of two or more nucleic acids, e.g., oligonucleotides and/or polynucleotides. "Template-mediated ligation" refers to ligation of two or more nucleic acids that are each bound or hybridized to a template. The nature of the bond or linkage may vary widely, and the ligation may be carried out enzymatically or chemically. A variety of template-mediated ligation reactions are described in the following references, which are incorporated by reference: U.S. Pat. No. 4,883,750; U.S. Pat. No. 5,476,930; U.S. Pat. No. 5,593,826; U.S. Pat. No. 5,426,180; U.S. Pat. No. 5,871,921.

A "label" is a composition detectable by spectroscopic, photochemical, biochemical, immunochemical, or chemical means. For example, useful labels include fluorescent dyes, electron-dense reagents, enzymes (e.g., as commonly used in an ELISA), biotin, digoxigenin, or haptens and proteins for which antisera or monoclonal antibodies are available. The label may be bound, either covalently or non-covalently, to a molecule. For example, a label may be bound to a tag and/or a ligand that binds a molecule or a tag, and more than one type of label can be bound to either or both of the tag and ligand. Thus, for example, an oligonucleotide tag can be covalently bound to a biotin group, where the oligonucleotide tag is then bound to a ligand that has a fluorescent label attached to the ligand.

As used herein, "nucleic acid" may include any polymer or oligomer of pyrimidine and purine bases, preferably cytosine (C), thymine (T), and uracil (U), and adenine (A) and guanine (G), respectively. (See Albert L. Lehninger, Principles of Biochemistry, at 793-800 (Worth Pub. 1982), the entire disclosure of which is incorporated herein by reference.) Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide may be a peptide nucleic acid (PNA). (See U.S. Pat. No. 6,156,501 the entire disclosure of which is incorporated herein by reference.)

As used herein, a "pool" refers to a physical mixture comprising a portion of two or more biological samples. A "pooled pool" refers to a physical mixture comprising a portion of each of two or more different pools.

A "maximum pool size" is a size that is approximately the maximum total number of biological samples that are or can be pooled together for reactions in the method. The "maximum pool size" may be determined by limitations arising from the steps of the method. For example, in some embodiments, two microparticles with different tags are added to a pool to identify attributes of a single biological sample. Thus, the number of biological samples that are pooled together is limited by the number of different microparticle tags that can be manufactured. The "maximum pool size" may be different for different reactions performed in the method, and the "maximum pool size" may be adjusted so that the method is efficient. In general, the "maximum pool size" is an indication of physical limits of the reactions that are performed in the method, but may be adjusted to more efficiently perform the method.

"Polynucleotide" and "oligonucleotide" are used interchangeably in this disclosure.

As used herein a "probe" or "capture probe" is defined as a nucleic acid capable of binding to a target nucleic acid of complementary sequence by one or more types of chemical interactions, usually complementary base pairing mediated by hydrogen bond formation. As used herein, a probe may include natural (i.e., A, G, U, C, or T) or modified bases (7-deazaguanosine, inosine, etc.) forming an oligomer by way of phosphodiester or other bonds that do not interfere with hybridization. Thus, probes may be peptide nucleic acids in which the constituent bases are joined by peptide bonds rather than phosphodiester linkages. In some embodiments, microparticles comprising at least one specific capture probe (e.g., a probe for one target nucleic acid) may be used. Microparticles may have one or more copies of each specific capture probe. In some embodiments, nucleic acid arrays comprising at least one capture probe may be used. An "anti-tag" refers to a probe that is capable of binding to a nucleic acid tag of complementary sequence.

The term "tag" refers to a molecule or portion thereof with a recognizable feature that allows it to be distinguished from other tag molecules, e.g., a distinguishable nucleotide or amino acid sequence, nucleotide or amino acid sequence length, shape, size, mass, color, optical density, differential absorbance or emission of light, chemical reactivity, magnetic or electronic properties and the like. Preferred examples of tags include tags comprising oligonucleotides (oligonucleotide tags) and fluorescers. A specific oligonucleotide tag may serve as to identify a sample or sequence, in the manner of a "barcode." A "tag" may include a florescent label so that the tag may be identified.

A "source tag" is a tag that is attached to a biological sample and identifies the source of the biological sample under study. In some embodiments, a source tag is or comprises an "oligonucleotide tag." In some embodiments, the source tag is a specific binding member comprising an oligonucleotide tag. Oligonucleotide tags may be identified by their nucleotide sequences. In some embodiments the oligonucleotide tag is a sequence of nucleotides selected such that the sequence does not duplicate a naturally-occurring sequence in the genome of the organism under study; such an oligonucleotide tag also is referred to as a "barcode."

A "marker tag," as used herein, is a tag that uniquely identifies an attribute. In some embodiments, the marker tag is the length of the reaction products, such a nucleic acid amplification products. In some embodiments, a marker tag is a tag that is attached to or comprises a polynucleotide or oligonucleotide and identifies an attribute under study. In some embodiments, a marker tag is or comprises an "oligonucleotide tag." In some embodiments, a marker tag comprises a specific binding member and an oligonucleotide tag. Oligonucleotide tags may be identified by their unique nucleotide sequences and can be barcodes. In some embodiments, the marker tag may identify an attribute under study by the length of the oligonucleotide tag. In some embodiments, the marker tag may identify an attribute by a fluorescent label.

The term "target" as used herein refers to a molecule that has an affinity for a given probe or specific binding member, or a segment of a particular molecule that has affinity for a probe or specific binding member. Targets may be naturally-occurring or man-made molecules. Examples of targets which can be employed by this invention include, but are not restricted to antigens, oligonucleotides and nucleic acids. A "target sequence" is a specific sequence of nucleotides of a target which is bound by a probe. A "target antigen" is a specific antigen, such as a specific cell surface marker, or a portion thereof, which is bound by a specific binding member.

"Target nucleic acid" or "template nucleic acid sequence" or "target nucleotide sequence" refers to a region of a nucleic acid that is to be either replicated, amplified, and/or detected, generally including the flanking sequences to which primers may be directed.

A "reaction product" is a product resulting from the reaction of two or more molecules. For instance, a "reaction product" of a biological sample and a source tag that comprises a specific binding member and an oligonucleotide tag refers to the complex formed when the specific binding member binds its cognate binding partner in the biological sample. In another example, by "reaction product" produced from a nucleic acid template is meant an amplification product, a transcription product, a reverse-transcription product, or any other nucleic acid product resulting from template-mediated nucleic acid synthesis.

The term "interrogating" as used herein refers to performing a process on reaction products that can be used to identify said reaction products in order to produce results that may be used to identify one or more attributes for one or more biological samples. "Identifying reaction products" refers to identifying the marker tags, and, if present, the source tags of the reaction products.

The term "unambiguous results" as used herein refers to results that can be used to determine an attribute for a biological sample. The term "result" as used herein refers to an outcome of interrogating reaction products.

The term "ambiguous results" as used herein refers to results that require additional steps in order to determine an attribute for a biological sample; in some embodiments two or more possible attributes, of two or more samples within a reaction, may have produced the same results.

As used herein, an "array" refers to an ordered array presented for binding to nucleic acids and the like. The term "array" encompasses the term "microarray." A nucleic acid array includes any two-dimensional or substantially two-dimensional (as well as a three-dimensional) arrangement of spatially or optically addressable regions bearing nucleic acids, particularly oligonucleotides or synthetic mimetics thereof, and the like. An array can comprise other materials, such as microparticle arrays. Where the arrays are arrays of nucleic acids, the nucleic acids may be adsorbed, physisorbed, chemisorbed, or covalently attached to the array substrate at any point or points along the nucleic acid chain. Arrays can be fabricated by conventional methods in the art, including drop deposition from pulse jets and photolithographic array fabrication. Such methods are described in detail in, for example, U.S. Pat. Nos. 6,242,266; 6,232,072; 6,180,351; 6,171,797; 6,323,043, and the references cited therein. These references are incorporated herein by reference.

An array is "addressable" when it has multiple regions of different moieties (e.g., different oligonucleotide sequences) such that a region (i.e., a "feature" or "spot" of the array) at a particular predetermined location (i.e., an "address") on the array will detect a particular sequence. Array features are typically, but need not be, separated by intervening spaces. In the case of an array in the context of the present application, the attribute-specific source-tagged reaction products can be detected by surface-bound capture probes which are bound to the substrate at the various regions.

A "scan region" refers to a contiguous (preferably, rectangular) area in which the array spots or features of interest are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded.

An "array layout" refers to one or more characteristics of the features, such as feature positioning on the substrate, one or more feature dimensions, and an indication of a moiety at a given location. An example is a "checkerboard array," which refers to the positioning of the features on the array in a checkerboard pattern.

As used herein a "molecular beacons" refers to single-stranded oligonucleotide hybridization probe that forms a stem-and-loop structure with an internally quenched fluorophore whose fluorescence is restored when the probe binds to a target nucleic acid sequence.

Materials Used in Method

The present invention is directed to identifying attributes of a plurality of biological samples. Exemplary biological samples for practicing the method include cells and sub-cellular materials. Cells include, but are not limited to, blood cells such as red blood cells (erythrocytes), white blood cells and platelets (thrombocytes). White blood cells include neutrophils, eosinophils, basophils, lymphocytes, monocytes, macrophages and dendritic cells. Other cells include epithelial cells such as buccal mucosa; and cells present in tissue samples such as biopsy samples, epidermal tissue samples, dermal tissue samples, and subcutaneous tissue samples. Sub-cellular materials of cells include but are not limited to mitochondria, nuclei, and genetic material such as chromosomal material and RNA such as mRNA, tRNA, miRNA, snRNA, and hnRNA.

Biological samples may be obtained from any living organism using conventional means known in the art. In a preferred embodiment, the biological sample is from a mammal, preferably a primate, and more preferably, a human.

The present invention contemplates sample preparation methods in certain embodiments. Biological material comprising cells may be cultured in vitro using standard methods known in the art to increase the number of cells. Biological material may also be processed so as to enrich and/or purify the sample for a particular component, such as red blood cells.

In embodiments directed to nucleic acid attributes, prior to or concurrently with the methods of analysis described herein, the information comprising a nucleotide sequence in a sample for analysis may be amplified using a variety of mechanisms, some of which may employ polymerase chain reaction (PCR). See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Manila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, each of which is incorporated herein by reference in their entireties for all purposes.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed PCR (CP-PCR) (U.S. Pat. No. 4,437,975), arbitrarily primed PCR (AP-PCR) (U.S. Pat. Nos. 5,413,909; and 5,861,245), degenerate oligonucleotide primed PCR (DOP-PCR) (Wells et al., 1999, Nuc Acids Res 27:1214-1218) and nucleic acid based sequence amplification (NABSA). (See, U.S. Pat. Nos. 5,409,818; 5,554,517; and 6,063,603, each of which is incorporated herein by reference). Other amplification methods that may be used are described in, U.S. Pat. Nos. 5,242,794; 5,494,810; 4,988,617; and 6,582,938, each of which is incorporated herein by reference.

In certain aspects of the invention, antigens or nucleic acid are detected by detecting one or more tags (also referred to as labels) attached to an antigen or nucleic acid, to molecules that bind to antigens or nucleic acids. The tag or label may be incorporated by any of a number of means well known to those of skill in the art. For instance, in one embodiment comprising detection of nucleic acid, the tag is simultaneously incorporated during the amplification step in the preparation of the sample nucleic acids. Thus, for example, PCR with labeled primers or labeled nucleotides will provide a labeled amplification product. In another embodiment, transcription amplification, as described above, using a labeled nucleotide (e.g., fluorescein-labeled UTP and/or CTP) incorporates a label into the transcribed nucleic acids.

Alternatively, a tag may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g., with a labeled RNA) by kinasing the nucleic acid and subsequent attachment (ligation) of a nucleic acid linker joining the sample nucleic acid to a label (e.g., a fluorophore).

In an embodiment comprising detection of an antigen, the tag or label may be coupled to a specific binding member such as an antibody or aptamer that can specifically bind to the antigen. In some embodiments, an oligonucleotide tag is bound to an antibody. In some embodiments, the antibody is a Fab or F(ab)$_2$. Methods for binding nucleic acid to polypeptides are known in the art.

The preparation and use of antibodies is well known in the art. See e.g. Harlow et al., 1988, Antibodies: A Laboratory Manual, Cold Spring Harbor, N.Y.; Harlow et al., 1999, Using Antibodies: A Laboratory Manual, Cold Spring Harbor Laboratory Press, NY.

The generation of polyclonal antibodies is accomplished by inoculating the desired animal with an antigen and isolating antibodies which specifically bind the antigen therefrom.

Monoclonal antibodies directed against an antigen may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Monoclonal antibodies directed against an antigen can be generated, for instance, from mice immunized with the antigen using standard procedures as referenced herein.

For use in preparing an antibody, an antigen may be purified from a biological source that endogenously comprises the antigen, or from a biological source recombinantly-engineered to produce or over-produce the antigen, using conventional methods known in the art. Exemplary protein sequences for the cell surface markers of various human cells are known in the art and readily accessible in public databases, such as National Library of Medicine's genetic sequence database GenBank® (Benson et al., 2008, *Nucleic Acids Research*, 36(Database issue):D25-30).

Nucleic acid encoding the monoclonal antibody obtained using the procedures described herein may be cloned and sequenced using technology which is available in the art, and is described, for example, in Wright et al. (1992, Critical Rev. Immunol. 12(3,4):125-168) and the references cited therein.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody may be engineered such that the protein is displayed on the surface thereof in such a manner that it is available for binding to the antigen against which the antibody is directed. Thus, when bacteriophage which express a specific antibody are incubated in the presence of the antigen, for instance, antigen immobilized on a resin or surface, the bacteriophage will bind to the antigen. Bacteriophage which do not express the antibody will not bind to the antigen. Such panning techniques are well known in the art and are described for example, in Wright et al., (supra). Processes, such as those described above, have also been developed for the production of human antibodies using M13 bacteriophage display (Burton et al., 1994, Adv. Immunol. 57:191-280).

The procedures just presented describe the generation of phage which encode the Fab portion of an antibody molecule. However, phage which encode single chain antibodies (scFv/phage antibody libraries) are also useful in preparing Fab molecules useful in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., (1991, J. Mol. Biol. 222:581-597). Panning of phage so generated for the isolation of a desired antibody is conducted in a manner similar to that described for phage libraries comprising Fab DNA. Synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105) may also be used to prepare an antibody useful in the practice of the invention.

Aptamers may be prepared using conventional methods known in the art. Nucleic acid aptamers may be prepared using SELEX ("Systematic Evolution of Ligands by Exponential Enrichment"). See, e.g., Ellington et al., (1990, Nature 346: 818-822); Tuerk et al., (1990, Science 249: 505-510); Stoltenburg et al., (2007, Biomol Eng. 2007 October; 24(4): 381-403. Epub 2007 Jun. 16); and Mairal et al. (2008, Anal Bioanal Chem. 390(4):989-1007. Epub 2007 Jun. 21) and references therein. Protein aptamers contain a a short variable peptide domain, which is attached at its two ends to a protein scaffold. Methods of preparing protein aptamers are known in the art. See, e.g., Crawford et al., (2003, Brief Funct Genomic Proteomic. 2(1):72-9) and Borghouts et al., (2008, Comb Chem High Throughput Screen. 11(2):135-45).

Detectable labels suitable for use in the present invention include any composition detectable by spectroscopic, photochemical, biochemical, immunochemical, electrical, optical or chemical means. Useful tags in the present invention include, but are not limited to: biotin for staining with labeled streptavidin conjugate; anti-biotin antibodies, magnetic beads (e.g., Dynabeads™); fluorescent dyes (e.g., fluorescein, texas red, rhodamine, green fluorescent protein, and the like); radiolabels (e.g., $^3H$, $^{125}I$, $^{35}S$, $^{4}C$, or $^{32}P$); phosphorescent labels; oligonucleotides; enzymes (e.g., horseradish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes. In some embodiments, a fluorescent dye is bound to a specific binding member to form a source tag or a marker tag.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Oligonucleotides can be detected by size and/or sequence. Detecting oligonucleotide size can be accomplished by an electrophoretic method such as capillary electrophoresis or by liquid chromatographic separation using an appropriate column medium.

In one embodiment, the label comprises a microparticle that may be color-encoded, such as described in U.S. Pat. No. 7,083,914, the entire disclosure of which is incorporated herein by reference. Color codes are assigned for the purpose of uniquely labeling members of a group of microparticles to preserve their chemical identity, thus the identity of microparticle-coupled antigen. Color codes are based on a set of encoding fluorophores of distinguishable wavelengths, excited-state lifetimes and levels of intensity, the latter controlled by adjusting the abundances of dyes. In an embodiment, the codes are interrogated to identify bound antigen.

Larger coding capacity for color coded particles may be provided by the use of optical gratings, associated with specific particles. Commercially available products includes VeraCode Technology (Illumina Inc., San Diego, Calif.). See also U.S. Pat. Nos. 7,858,307 and 7,871,770.

In certain embodiments of the invention, polynucleotide hybridization assays are conducted. Hybridization assay procedures and conditions will vary depending on the application and are selected in accordance with the general binding methods known including those referred to in: Sambrook et al. Molecular Cloning: A Laboratory Manual ($3^{rd}$ edition, Cold Spring Harbor Laboratory Press, Cold Spring Harbor, N.Y., 2001); Berger and Kimmel, Methods in Enzymology, Vol.

152, Guide to Molecular Cloning Techniques (Academic Press, Inc., San Diego, Calif., 1987); Young and Davism, (1983) Proc. Natl. Acad. Sci USA, 80: 1194. Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference. In an embodiment wherein source tags comprise an oligonucleotide tag, hybridization to a nucleic acid array can be conducted. In an embodiment, the nucleic acid features of the array are spatially arranged in the form a checkerboard. In another embodiment, source and/marker tags comprising oligonucleotide tags can be hybridized to anti-tags as part of a detection procedure.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in PCT Application PCT/US99/06097 (published as WO99/47964), each of which also is hereby incorporated by reference in its entirety for all purposes.

In some embodiments of the invention, the source tags utilized in the practice of the invention comprise oligonucleotide tags. In some embodiments, an oligonucleotide tag is attached to the 3'- or 5'-end of the a polynucleotide, or is incorporated into a reaction product, e.g. polymerase reaction product, which uses the polynucleotide as a template. In other embodiments, the oligonucleotide tag is bound to a specific binding member. In an embodiment, the source tag comprises an oligonucleotide tag bound to an antibody.

Oligonucleotide tags may vary widely in size and compositions; the following references provide guidance for selecting sets of oligonucleotide tags appropriate for particular embodiments. See U.S. Pat. No. 5,635,400; Brenner et al., Proc. Natl. Acad. Sci., 97: 1665-1670 (2000); European patent publication 0 303 459; Shoemaker et al., Nature Genetics, 14: 450-456 (1996); European patent publication 0799897A1; and U.S. Pat. No. 5,981,179; the entire disclosures of which are incorporated herein by reference. In one aspect, oligonucleotide tags can each have a length within a range of from 2 to 36 nucleotides, or from 4 to 30 nucleotides, or from 8 to 20 nucleotides, respectively. A set of oligonucleotide tags may have a size in the range of from several tens to many thousands, or even millions. Preferably, the nucleotide sequence of the oligonucleotide tag is a sequence selected such that it is distinguishable from human genomic sequences, i.e., the oligonucleotide tags comprise barcodes.

Methods for binding an oligonucleotide to an antibody or an aptamer are known in the art. For instance, Kozlov et al., (2004, Biopolymers 73(5):621-630) describe methods of chemically conjugating oligonucleotides to antibodies. Oligonucleotides can also be bound non-covalently to antibodies by means of high affinity binding partners such as biotin and avidin. In an embodiment, avidin is attached to an antibody via preparation of a fusion protein, such as by a recombinant expression construct linking the coding sequence for an antibody and the coding sequence for avidin. Expression of the construct produces a fusion protein comprising an antibody and avidin. Biotinylated oligonucleotides can then bind to the fusion protein. Methods for preparing recombinant expression construct and expressing such constructs are well known in the art. See, for instance, Sambrook et al. (2001, Molecular Cloning: A Laboratory Manual, $3^{rd}$ edition, Cold Spring Harbor Laboratory Press, Cold Spring Harbor, N.Y.); Ausubel et al. (eds., 2005, Current Protocols in Molecular Biology, John Wiley & Sons, New York); and Gerhardt et al. (eds., 1994, Methods for General and Molecular Bacteriology, American Society for Microbiology, Washington, D.C.).

Biotinylated oligonucleotides may also be bound non-covalently to antibodies comprising an immunoglobulin G Fc portion by means of a protein A-streptavidin fusion linker. Biotin-avidin chemistries, for instance to prepare biotinylated oligonucleotides, are well known in the art. See, for instance, Savage at al. (1992) "Biotin-Avidin Chemistry: A Handbook," Pierce Chemical Co., Rockford, Ill. Methods for coupling or incorporating other types of labels into polypeptides are also well known in the art. See, for instance, Niemeyer et al., (2005, Trends in Biotechnology 23(4):208-216) and references cited therein.

As will be appreciated by those in the art, the attachment, or joining, of an oligonucleotide tag to a polynucleotide can be done in a variety of ways. In an embodiment, the sequence of the oligonucleotide tag is incorporated into the nucleotide sequence of primers of the reaction (extension primers, amplification primers, readout probes, genotyping primers, Rolling Circle primers, etc.) during the chemical synthesis of the primers. The tag then is incorporated in the reaction product formed in a primer-extension reaction, i.e., polymerase chain reaction, to form reaction product that now contains the tag sequence. Alternatively, the tag sequences can be added enzymatically. Furthermore, the tag can be attached to the target after synthesis; this post-synthesis attachment can be either covalent or non-covalent.

An oligonucleotide tag may be joined to a polynucleotide by a ligation method, i.e., formation a covalent bond or linkage between the termini of the oligonucleotide tag and polynucleotide in a template-driven reaction. The nature of the bond or linkage may vary widely and the ligation may be carried out enzymatically or chemically. A variety of template-driven ligation reactions are described in the following, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al., Methods in Enzymology, 68: 50-71 (1979); Engler et al., The Enzymes, 15: 3-29 (1982); and Namsaraev, U.S. patent publication 2004/0110213.

In one embodiment of the invention, electrophoretic tags, or "e-tags," that are incorporated into nucleic acid molecules are used as source tags or marker tags, such as described in U.S. Pat. No. 7,312,034, the entire disclosure of which is incorporated by reference. In practicing the method, a source tag and/or marker tag comprises an oligonucleotide sequence that is unique. After binding the source and/or marker tag to a biological sample, the samples are reacted under hybridization conditions with a set of electrophoretic tag (e-tag) probes, each having (i) an oligonucleotide target-binding portion or moiety that is complementary to one of the source and/or marker tag sequences, (ii) an electrophoretic probe having separation characteristics, e.g., electrophoretic mobility, that is unique to a given extension sequence, and (iii) a linker joining the oligonucleotide portion and the electrophoretic probe, where the linker is cleavable under selected conditions when the oligonucleotide portion of the probe is bound to a complementary target extension sequence. The target sequences with bound e-tag probes are treated under the selected conditions, to release an e-tag reporter from each e-tag probe bound to a target sequence, the released reporters are separated, e.g., electrophoretically, and the separated reporters are detected, to identify the source tag and/or marker tag that hybridized to the probes.

In some embodiments, tags and/or labels may be attached to solid phase supports, e.g., microparticles. Molecules such as oligonucleotides, proteins, aptamers and small organic molecules may be coupled to microparticles in accordance with any of the known coupling reactions in the art. See e.g., G. T. Hermanson, Bioconjugate Techniques (Academic Press, 1996) and Illum et al., Methods in Enzymology 112: 67-84 (1985), the entire disclosures of which are incorporated herein by reference.

Embodiments of the Method

The present invention provides a method of identifying attributes for at least two biological samples in a plurality of biological samples. In particular, the method identifies multiple attributes having unequal properties for each of two or more biological samples in a plurality of biological samples. Examples of properties include, but are not limited to, frequency of occurrence, e.g., frequency of one allele of a polymorphic site in a gene, frequency of an allele encoding an antigen, or frequency of a blood group antigen on a cell surface, and level of expression. Broadly, as depicted in FIG. 1, the method 50 comprises a step of partitioning attributes 100 and a step of group testing 200. "Partitioning attributes" refers generally to segmenting or sorting attributes into different categories of subsets based in part on the unequal property of the attribute. "Group testing" refers to identifying one or more specific attributes in a common mixture comprising a plurality of biological samples. In some instances, two or more attributes having the same or similar categorization are assessed in the same common mixture and may be said to be "binned" together. The method provides several advantages, such as a reduction in requisite processing.

As envisioned in the present invention with respect to the disclosed methods and compositions of matter, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

Exemplary embodiments of the method include: identifying antigens such as cell surface markers; and identifying alleles of polymorphic sites. In a preferred embodiment, the attributes identified according to the method are antigens. Exemplary cell surface markers include blood antigens or human leukocyte antigens (HLA). "Identifying antigens" as used herein excludes identifying alleles of polymorphic sites.

Identifying Blood Group Antigens of Red Blood Cells ("d"=1; Two Blood Group Antigens)

An embodiment pertaining to identifying attributes of a red blood cell for a plurality of samples is now described. In this embodiment, the attribute to be identified is an antigen, specifically a blood antigen present on the surface of a blood cell for different blood groups. This embodiment can be useful to characterize antigens of possible donor blood samples in comparison to antigens of a recipient.

Figures 2A, 2B:
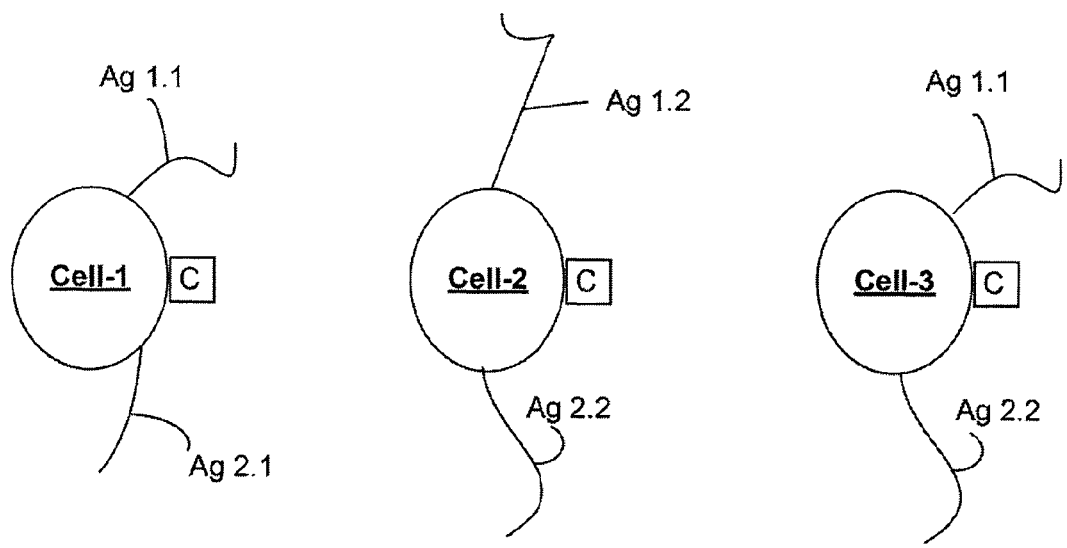
FIG. 2A schematically illustrates three biological samples, Cell-1, Cell-2, Cell-3.
FIG. 2B schematically illustrates an attribute profile for the three biological samples, Cell-1, Cell-2, Cell-3, illustrated in FIG. 2A.

FIG. 2A schematically illustrates three cells, designated Cell-1, Cell-2, and Cell-3. The cells have two different blood antigen types or groups present on their cell surface. Each antigen group has two different possible antigens, therefore there are a total of four attributes. Thus, the attributes displayed on the surface of Cell-1 are antigen 1 of antigen group 1 ("Ag 1.1") and antigen 1 of antigen group 2 ("Ag 2.1"). The attributes displayed on the surface of Cell-2 are antigen 2 of antigen group 1 ("Ag 1.2") and antigen 2 of antigen group 2. The attributes displayed on Cell-3 are antigen 1 of antigen group 1 ("Ag 1.1") and antigen 2 of antigen group 2 ("Ag 2.2"). The cells also have a common cell surface marker C, which is present on all the cells of interest in the plurality of biological samples. Common cell surface markers are discussed below. The attribute profiles for these three cells are depicted in FIG. 2B.

Figure 3:
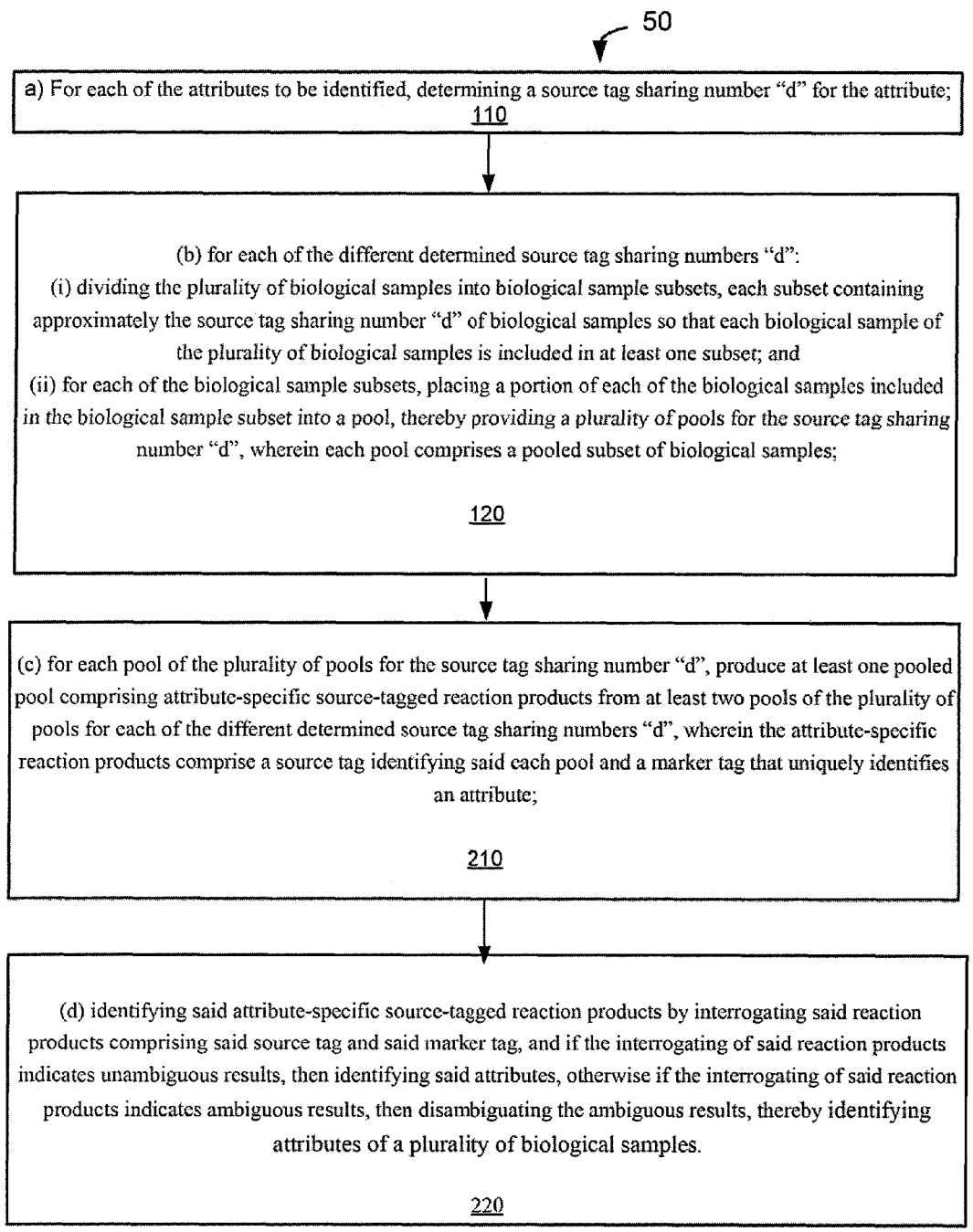
FIG. 3 schematically illustrates an embodiment of the method of determining an attribute profile for a plurality of biological samples.

FIG. 3 illustrates an embodiment of a method 50 of identifying a plurality of cell surface markers of a plurality of biological samples. The samples of the plurality may be sourced from different individuals. Alternatively, the samples of the plurality may be sourced from the same individual under different conditions, such as different points of time, different therapeutic regimens and/or different states of disease. FIGS. 4-7 illustrate additional details of the embodiment of FIG. 3.

The method 50 of FIG. 3 begins with step 110 (a): for each of the attributes to be identified, determining a source tag sharing number "d" for the attribute. In particular, a source tag sharing number, "d", is determined for an attribute; "d" represents an approximate number of biological samples from different sources that may share a source tag in the process for determining the attribute, This process, source tags, the selection of source tag sharing numbers "d", and binning are described in greater detail below. For purposes of illustration, a source tag sharing number of "d"=1 will be used for all the attributes for the following example. Other examples, described in detail below, illustrate the case d>1, that is source tag sharing numbers exceeding 1. For the first example of method 50 which is illustrated in FIG. 3, the source tag sharing number "d"=1 for Ag 1.1, Ag 1.2, Ag 2.1 and Ag 2.2. The source tag sharing numbers may not necessarily be determined explicitly, but implicitly by the number of biological source samples sharing source tags in the steps of method 50.

The method 50 of FIG. 3 continues with step 120 (b): for each of the different determined source tag sharing numbers "d": (i) dividing the plurality of biological samples into sample subsets, each subset containing approximately the source tag sharing number "d" of biological samples so that each biological sample of the plurality of biological samples is included in at least one subset. Here, as discussed above, for this example of the method 50, the source tag sharing number "d"=1 is used for each of the four attributes, Ag 1.1, Ag 1.2, Ag 2.1, and Ag 2.2. In this example, the plurality of biological samples is three (3). So, the three biological samples, Cell-1, Cell-2, and Cell-3, are divided into three subsets, each subset comprising one (1) biological sample.

Figure 8:
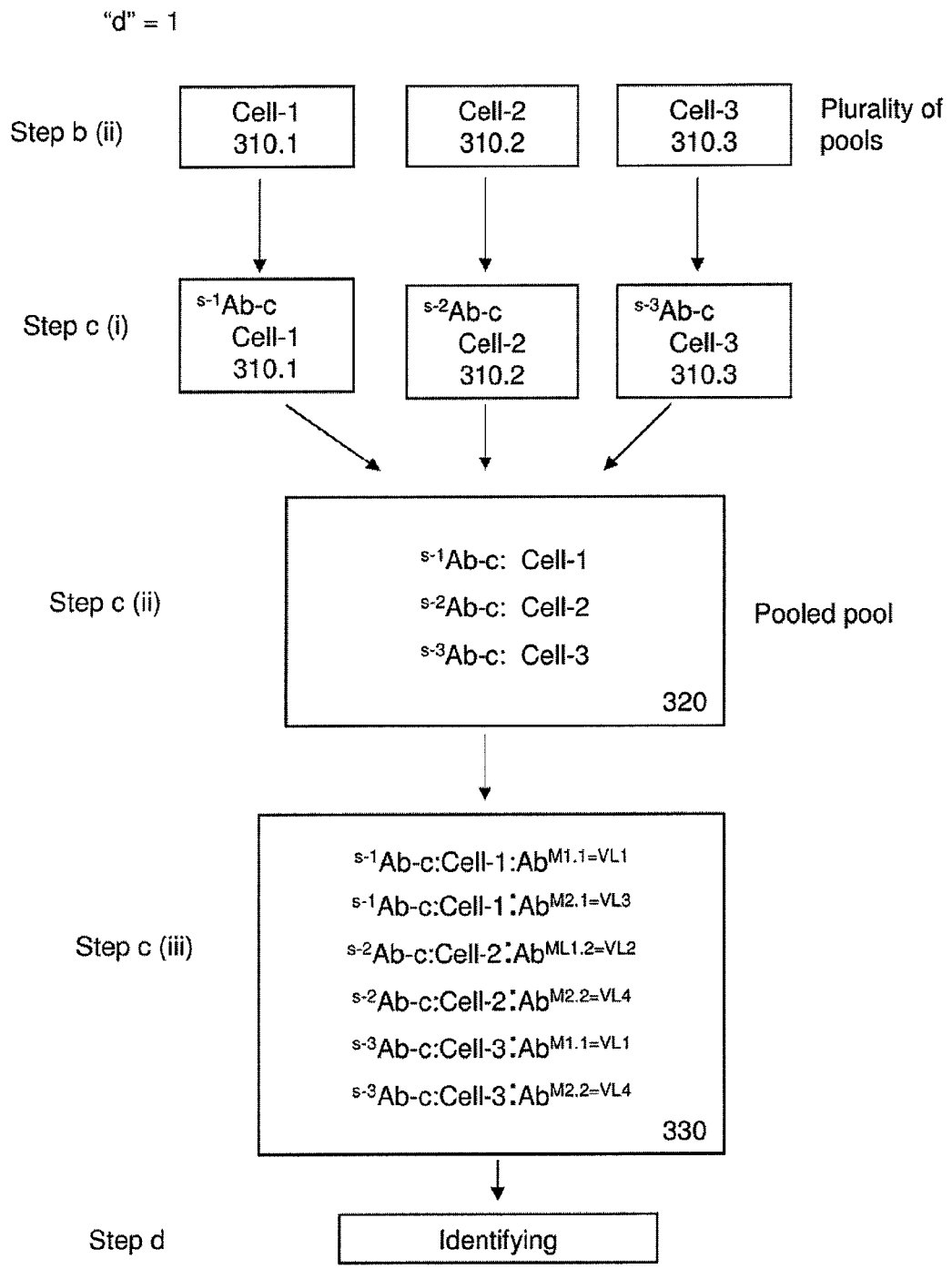
FIG. 8 schematically illustrates the operation of an embodiment of the method illustrated in FIG. 3 for the case where step 210 is carried out as shown in FIG. 4 (step 210.1)

Step 120 (b) continues with (ii): for each of the biological sample subsets, placing a portion of each of the biological samples included in the sample subset into a pool, thereby providing a plurality of pools for the source tag sharing number "d", wherein each pool comprises a pooled subset of biological samples. Here, there are three biological sample subsets, each having one biological sample. As illustrated in FIG. 8, a portion of biological sample Cell-1 is placed in pool 310.1, a portion of biological sample Cell-2 is placed in pool 310.2, and a portion of biological sample Cell-3 is placed in pool 310.3. The plurality of pools for source tag sharing number "d"=1 is thus represented by the group comprising 310.1, 310.2, and 310.3.

Method 50 in FIG. 3 continues with step 210 (c): for each pool of the plurality of pools for the source tag sharing number "d," produce at least one pooled pool comprising attribute-specific source-tagged reaction products from at least two pools of the plurality of pools for each of the different determined source tag sharing numbers "d," wherein the attribute-specific source-tagged reaction products comprise a source tag identifying said each pool and a marker tag uniquely identifying an attribute. Step 210 (*c*) can be carried out in a number of different embodiments. FIGS. 4-7 illustrate different embodiments for producing at least one pooled pool comprising attribute-specific source-tagged reaction products.

The embodiment illustrated in FIG. 4 depicts step 210.1 (*c*) comprising (i): performing a reaction in the pool to produce source-tagged reaction products comprising a source tag identifying said each pool.

As described previously, a source tag can comprise a specific binding member that specifically binds to a cognate binding partner, for instance, a cell surface antigen that is common to all of the target components of the biological samples. By "common to all of the target components of the biological samples" is meant either an antigen which is present on substantially all the material in a biological sample or on components of interest in the biological sample, or a group of antigens wherein each target component has at least one of the antigens in the group present. In a biological sample comprising intact blood cells, for instance, the common surface marker can be present on all blood cells. The common target can be present only on a subset of interest, such as T-lymphocytes. An exemplary common surface marker for a biological sample comprising intact cells is phospholipid. Accordingly, a specific binding member that binds phospholipid can comprise part of the source tag for preparing source-tagged cells. An exemplary surface marker common to leukocytes is CD45, and a surface marker common to T-lymphocytes is CD8. These examples of common surface markers are non-limiting. The art is replete with information about cell surface markers that are common to specific cell types. See, e.g., the online database from the Human Cell Differentiation Molecules (HCDM) organization, available at www(dot)hcdm(dot)org. Other disclosures of cell surface markers include Zola et al. (2007, J Immunol Methods 319 (1-2):1-5, Epub 2006 Dec. 4); Matesanz-Isabel et al. (2011, Immunol Lett. 134(2):104-112). Thus, the skilled artisan is readily able to identify appropriate common surface markers for practicing the method of the invention.

In one embodiment, an oligonucleotide tag is bound to the specific binding member to produce a source tag. Each pool can have a unique oligonucleotide tag assigned to it such that identification of the oligonucleotide tag serves to identify the pool in which the biological sample came from. In an embodiment, the oligonucleotide tag is identified, in a later step, by means of a checkerboard array. Each square of the checkerboard contains multiple copies of a capture probe that is complementary to one of the oligonucleotide tags used as source tags. The spatial position of a given source-tagged sample on the checkerboard thus serves to identify the source tag (e.g., an addressable array).

In another embodiment, the oligonucleotide tag is identified, in a later step, by means of microparticles having an attached capture probe complementary to a source tag. The microparticles further comprise a fluorescent label or mixture of such labels that identifies the capture probes attached to the microparticles.

In another embodiment, the tag itself is a fluorescent tag. Each source tag has a different fluorescent tag bound to it. In this embodiment, detection of the source tag, in a later step, can be by means of flow cytometry or fluorescence microscopy.

Figure 10:
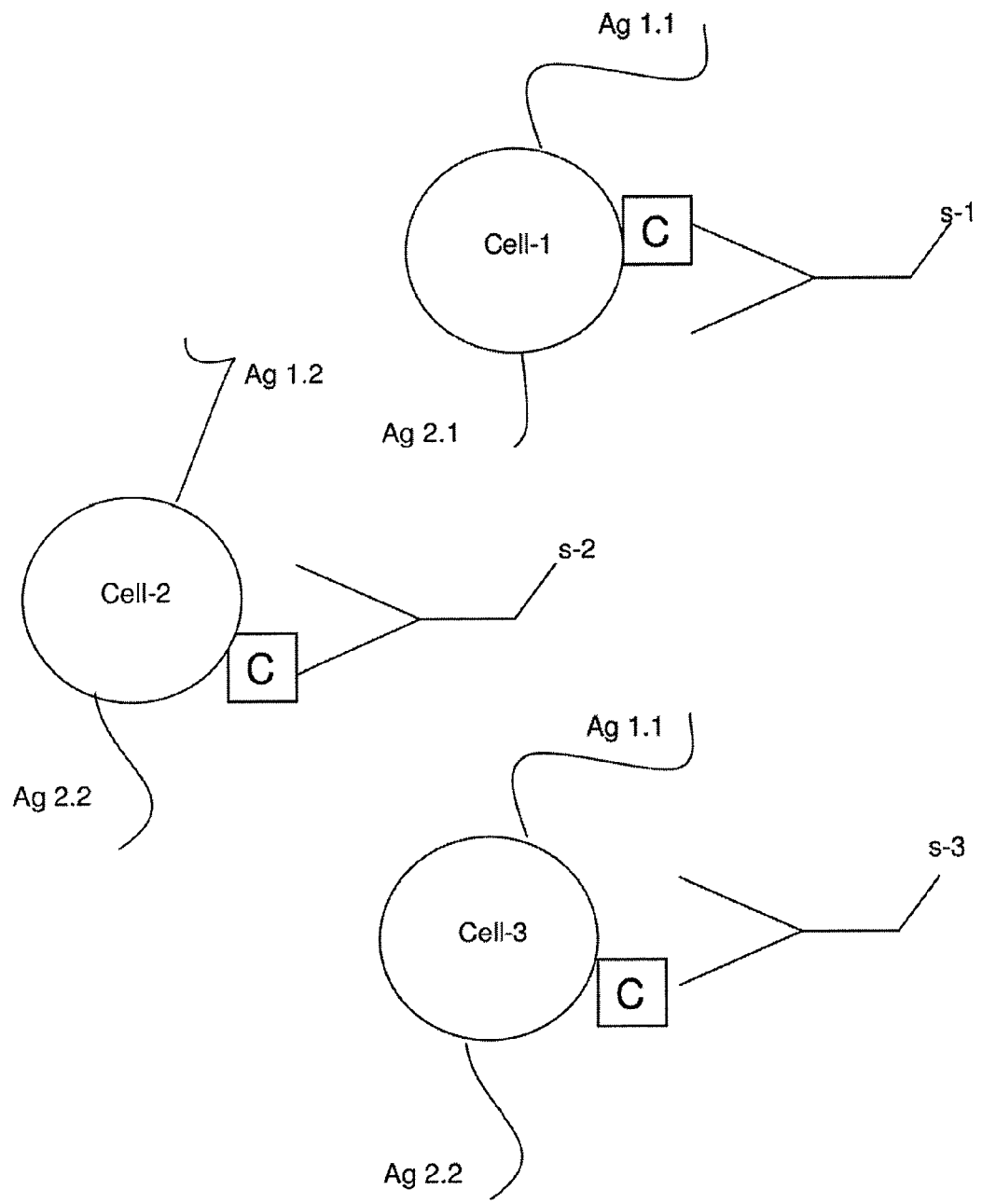
FIG. 10 schematically illustrates source-tagged reaction products.

For pools 310.1, 310.2 and 310.3 in the present example, therefore, three source tags are prepared. As depicted schematically in FIG. 9, the source tags comprise a specific binding member Ab-c, such as an antibody, and one of three different tag, s-1, s-2 and s-3, to produce $^{s-1}$Ab-c, $^{s-2}$Ab-c, and $^{s-3}$Ab-c. Specific binding member Ab-c binds to antigen C, which is present on all of the cells. For ease of illustration, specific binding member Ab-c is depicted as binding a single antigen C. Antibodies generally comprise at least two antigen binding domains (e.g., Immunoglobulin G), therefore, a single antibody may be bound to more than one antigen at the same time. As illustrated in FIG. 8, a source tag, such as $^{s-1}$Ab-c, is combined with a pool, such as 310.1, under conditions suitable to allow binding of the specific binding member to the common antigen to produce source-tagged reaction products. Preferably the conditions do not adversely affect the structural integrity of the attributes to be identified or at the structural integrity of the target of the marker tag, discussed below. Preferably the conditions also minimize non-specific binding of the binding member to antigens other than the common antigen. Determining suitable conditions for binding is common in the art for the skilled artisan. The result of the binding reaction is source-tagged reaction products, as schematically shown in FIG. 10, wherein the source tag on a reaction product indicates the pool in which the reaction product was prepared. As discussed below, for source tag sharing numbers greater than 1 (i.e., d>1), more than one biological sample may be placed in each pool.

Step 210.1 (*c*) of FIG. 4 continues with (ii): pooling in at least one pooled pool at least some of the said produced source-tagged reaction products from at least two pools of the plurality of pools for the source tag sharing number "d", thereby providing a plurality of pooled pools comprising at least one pooled pool for each of the different determined source tag sharing numbers "d." The source-tagged reaction products may be pooled by physically combining aliquots of the source samples comprising source-tagged reaction products $^{s-1}$Cell-1, $^{s-2}$Cell-2, and $^{s-3}$Cell-3 into pooled pool 320, as illustrated in FIG. 8.

As depicted in FIG. 8, step 210.1 (*c*) of FIG. 4 continues with (iii): for each of the attributes to be identified, performing a second reaction using the source-tagged reaction products to produce attribute-specific source-tagged reaction products comprising a marker tag. The marker tag indicates a specific attribute. As depicted in FIG. 8, the second reaction may be in the pooled pool 320 for the source tag sharing number "d", the "d" corresponding to the source tag sharing number "d" determined for the attribute in step (a).

A marker tag uniquely identifies an attribute. In some embodiments, the marker tag comprises a specific binding member that binds to an antigen and a fluorescent tag bound to the specific binding member. The specific binding member specifically binds to the target antigen which is the attribute to be identified. In an embodiment, the specific binding member is an antibody. The fluorescent tag is unique to the marker tag, thereby enabling identification of the attribute by detecting the fluorescent tag.

Figure 11:
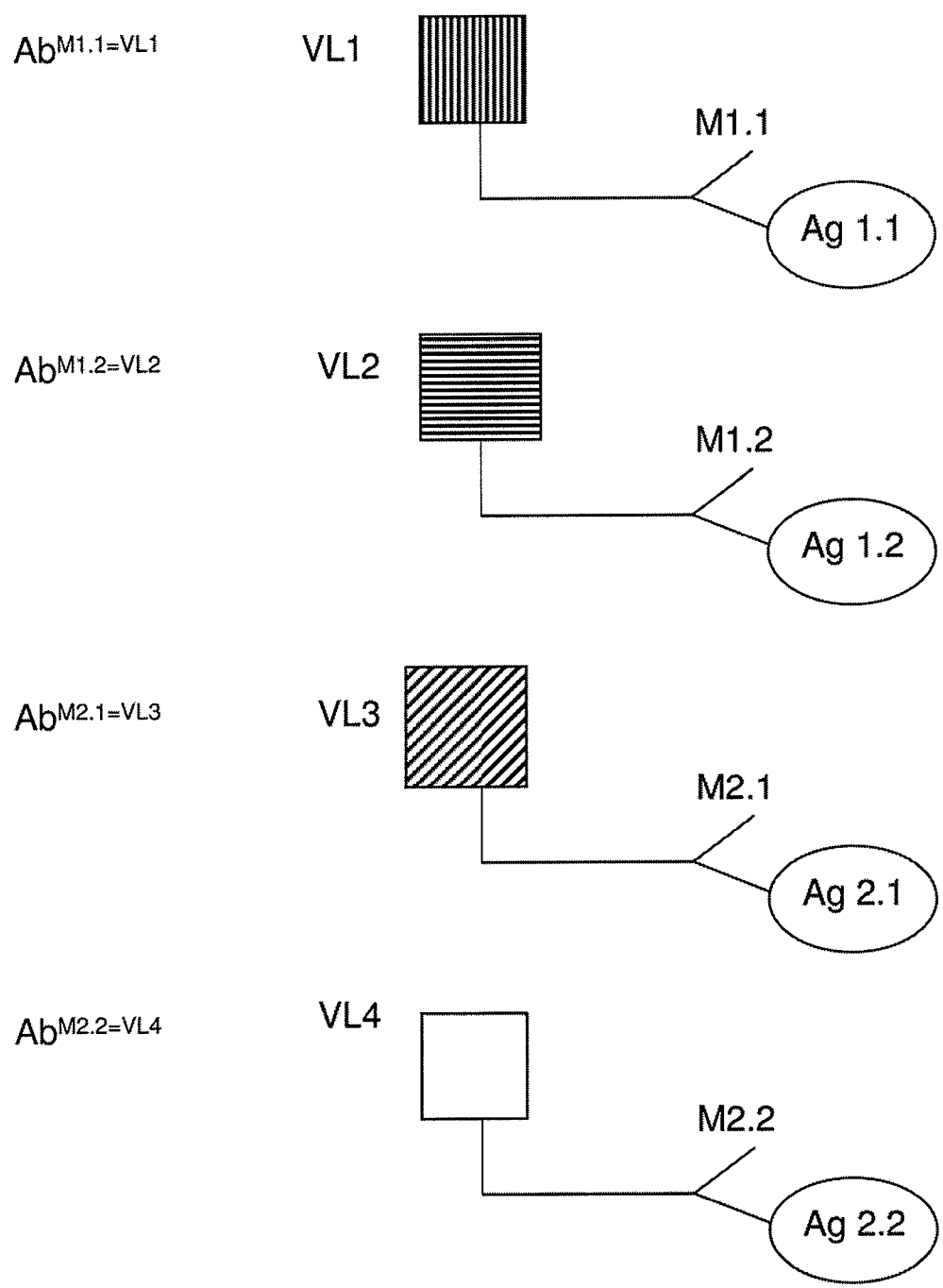
FIG. 11 schematically illustrates attribute-specific marker tags comprising visual labels ("VL") bound to a specific binding member that binds to a target antigen (an attribute to be identified)

FIG. 11 illustrates schematically four marker tags, Ab$^{M1.1=VL1}$, Ab$^{M1.2=VL2}$, Ab$^{M2.1=VL3}$, and Ab$^{M2.2=VL4}$. Marker tag Ab$^{M1.1=VL1}$ comprises a specific binding member Ab$^{M1.1}$ that binds antigen 1.1 and a visual label VL1. Marker tag Ab$^{M1.2=VL1}$ comprises a specific binding member Ab$^{M1.2}$ that binds antigen 1.2 and a visual label VL2. The pattern is the same for the marker tags for antigens 2.1 and 2.2. The four marker tags are added to pooled pool 320 depicted in FIG. 8 to perform the second reaction of binding marker tags to produce the attribute-specific source-tagged reaction products of pooled pool 330, under conditions suitable to allow binding of the specific binding members of the marker tags to the attributes. Preferably the conditions do not adversely affect the structural integrity of the attributes to be identified, the structural integrity of the target of the marker tag, or disrupt the binding of the source tag to the common antigen. Preferably the conditions minimize non-specific binding. As discussed above regarding source tags, determining suitable conditions is standard in the art.

Figure 12:
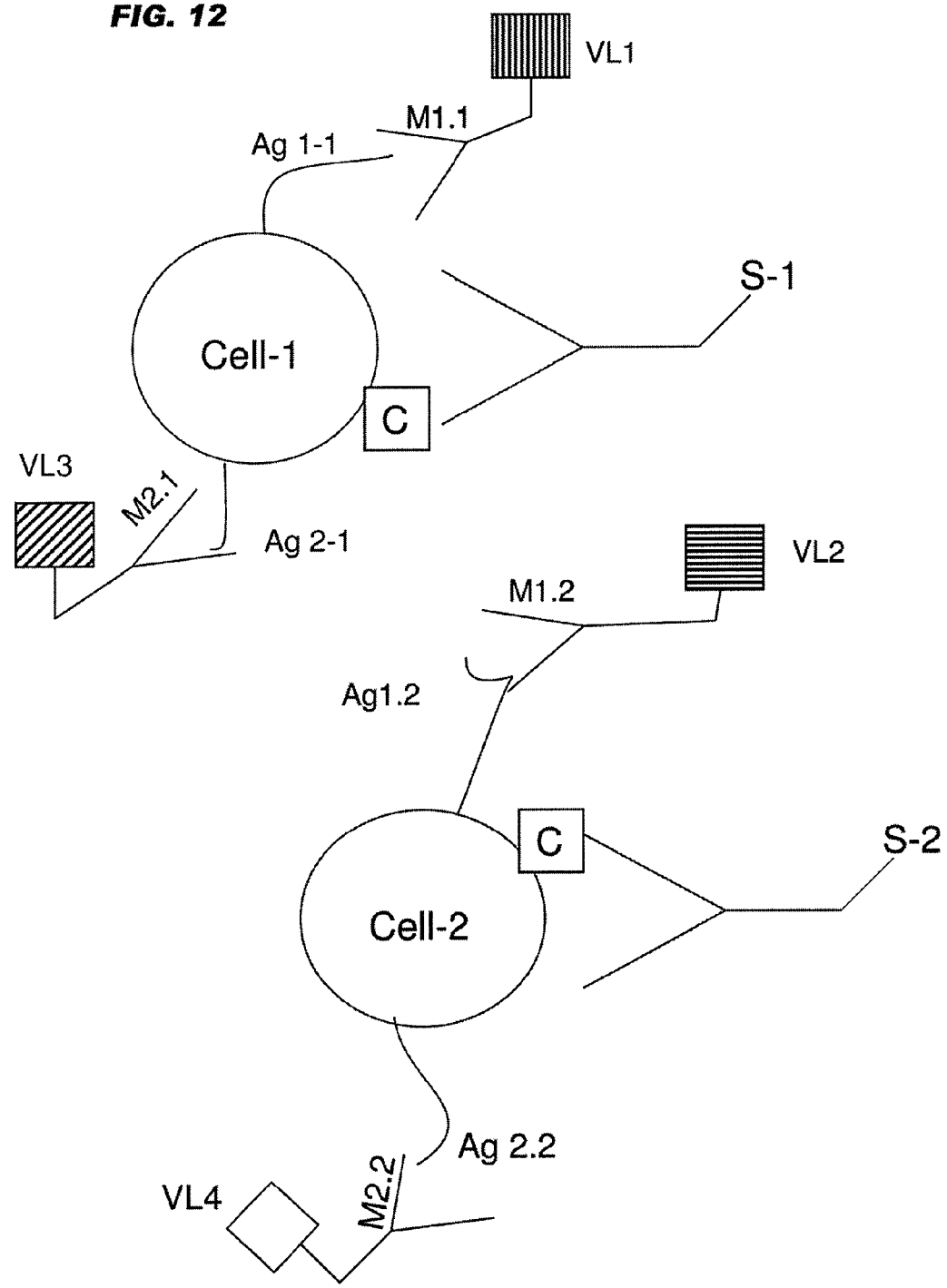
FIG. 12 schematically illustrates attribute-specific source tagged reaction products.
Figure 12:
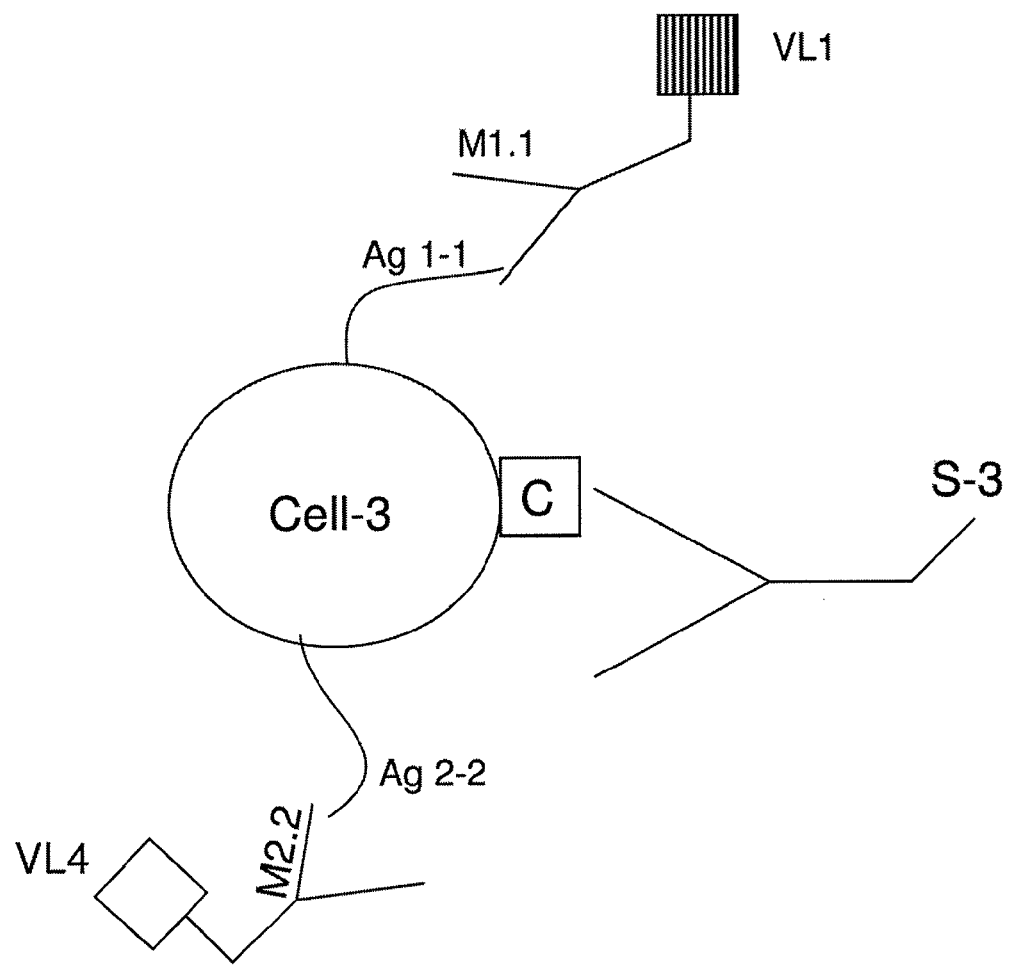

FIG. 12 schematically illustrates attribute-specific source tagged reactions products for Cell-1, Cell-2 and Cell-3. As shown, if interrogating more than one blood group type in a pool, more than one marker tag type can bind to a biological sample. For instance, Cell-1 comprises two attributes to be identified, Ag 1.1 and Ag 2.1. The attribute-specific reaction product for Cell-1 therefore can comprise the source tag $^{s-1}$Ab-c (bound to the antigen common to the biological samples), a marker tag Ab$^{M1.1=VL1}$ for Ag 1.1 and a marker tag Ab$^{M2.1=VL3}$ for Ag 2.1. The attribute-specific reaction product for Cell-2 therefore can comprise the source tag $^{s-2}$Ab-c (bound to the antigen common to the biological samples), a marker tag Ab$^{M1.2=VL2}$ for Ag 1.2 and a marker tag Ab$^{M2.2=VL4}$ for Ag 2.2. Similarly, the attribute-specific reaction product for Cell-3 therefore can comprise the source tag $^{s-3}$Ab-c (bound to the antigen common to the biological samples), a marker tag Ab$^{M1.1=VL1}$ for Ag 1.1 and a marker tag Ab$^{M2.2=VL4}$ for Ag 2.2. Thus, the embodiment illustrated in FIG. 4 can be carried out.

FIGS. 5-7 illustrate other embodiments for producing at least one pooled pool comprising attribute-specific source-tagged reaction products. In these embodiments, the order of the steps is different compared to the embodiment illustrated in FIG. 4 step 210.1 (c). Considerations of the binding conditions in these are embodiments are comparable to what is discussed for the embodiment depicted in FIG. 4.

FIG. 5 depicts step 210.2 (c). In this embodiment of method 50 of FIG. 3, a pooled pool comprising attribute-specific source-tagged reaction products is prepared by first source tagging biological samples in a pool and then reacting with a marker tag, prior to forming pooled pools. Accordingly, step 210.2 (c) comprises (i): performing a reaction in the pool to produce source-tagged reaction products comprising a source tag identifying said each pool; followed by (ii): for each of the alleles to be identified, performing a second reaction using said source-tagged reaction products to produce attribute-specific source-tagged reaction products comprising a marker tag, wherein said marker tag uniquely identifies an attribute. Step 210.2(c) continues with (iii): pooling in at least one pooled pool at least some of the said attribute-specific source-tagged reaction products from at least two pools of the plurality of pools for the source tag sharing number "d," thereby providing a plurality of pooled pools comprising at least one pooled pool for each of the different determined source tag sharing numbers "d."

FIG. 6 depicts step 210.3 (c). In this embodiment of method 50 of FIG. 3, a pooled pool comprising attribute-specific source-tagged reaction products is prepared by first reacting biological samples with a marker tag, then source tagging the biological samples, prior to forming pooled pools. Accordingly, step 210.3 (c) comprises (i): for each of the attributes to be identified, performing a reaction in the pool using said biological samples to produce attribute-specific reaction products comprising a marker tag, wherein said marker tag uniquely identifies an attribute, followed by (ii): performing a second reaction in the pool using said attribute-specific reaction products to produce attribute-specific source-tagged reaction products comprising a source tag identifying said each pool. Step 210.3 (c) then continues with (iii): pooling in at least one pooled pool at least some of the said attribute-specific source-tagged reaction products from at least two pools of the plurality of pools for the source tag sharing number "d," thereby providing a plurality of pooled pools comprising at least one pooled pool for each of the different determined source tag sharing numbers "d."

FIG. 7 depicts 210.4 (c). In this embodiment of method 50 of FIG. 3, a pooled pool comprising attribute-specific source-tagged reaction products is prepared for each pool of the plurality of pools for the source tag sharing number "d" by reacting a marker tag and reacting a source tag with a pool of biological samples in the same step. In other words, the source tag and the marker tag are combined with a pool comprising a pooled subset of biological samples substantially concurrently; therefore, the two binding reactions can occur substantially concurrently in a pool. This step is then followed by pooling to form pooled pools. Thus, step 210.4 (c) comprises (i): for each of the attributes to be identified, performing a reaction in the pool using said biological samples to produce attribute-specific source-tagged reaction products comprising a marker tag and a source tag, wherein said marker tag uniquely identifies an attribute and said source tag identifying said each pool. Step 210.4 (c) continues with (ii): pooling in at least one pooled pool at least some of the said attribute-specific source-tagged reaction products from at least two pools of the plurality of pools for the source tag sharing number "d", thereby providing a plurality of pooled pools comprising at least one pooled pool for each of the different determined source tag sharing numbers "d."

Returning to FIG. 3 and FIG. 8, method 50 continues with step 220 (d): identifying the attribute-specific source-tagged reaction products by interrogating the reaction products comprising the source tag and the marker tag. If the interrogating of the reaction products indicates unambiguous results, then the attributes are identified. If interrogating the reaction products indicates ambiguous results, then the ambiguous results are disambiguated.

Figure 13A:
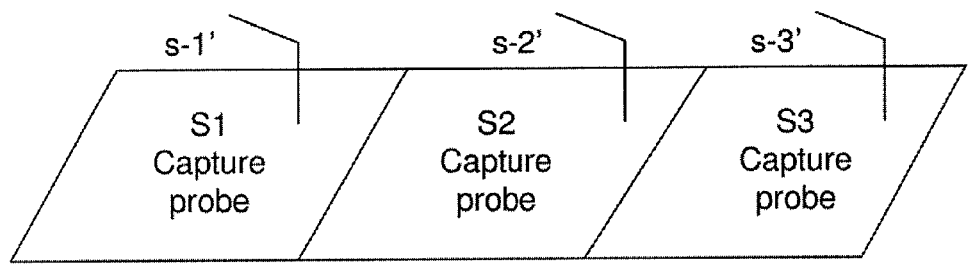
FIG. 13A schematically illustrates a checkerboard array comprising capture probes for source tags s-1, s-2 and s-3, respectively labeled s-1', s-2' and s-3'.
Figure 13B:
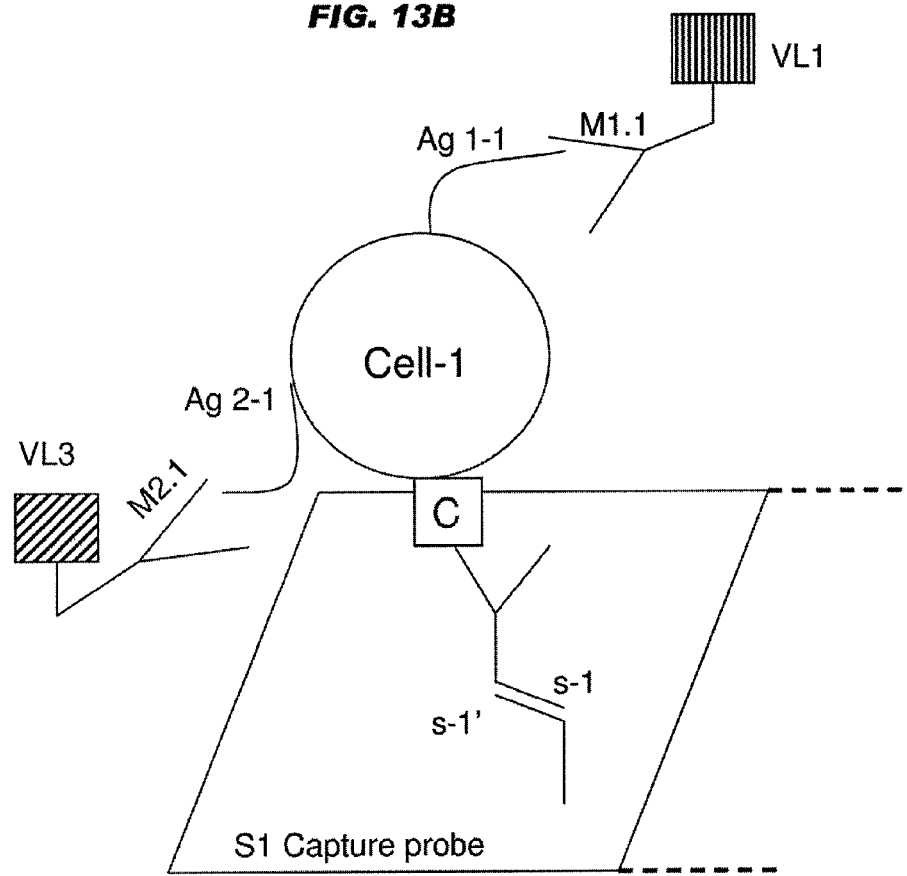
FIG. 13B schematically illustrates an attribute-specific source-tagged reaction product comprising source tag s-1 bound to a capture probe for s-1 in a checkerboard array.

Interrogation of the reaction products can be accomplished in a variety of ways. In the embodiment depicted in FIGS. 13A and 13B, the attribute-specific source tagged reaction products are identified by use of a checkerboard array. In this embodiment, each source tag comprises an oligonucleotide tag that is complementary to a capture probe in one of the squares of the checkerboard array. As depicted in FIG. 13A, one region of the array comprises s-1', the capture probe for source tag s-1. Another region of the array comprises s-2', the capture probe for source tag s-2; and a third region comprises s-3', the capture probe for source tag s-3. The source tag is therefore identified by the spatial location (i.e., address) on the array where the attribute-specific source-tagged reaction product binds. The marker tags comprise fluorescent tags. Thus, the attributes are then identified by imaging the array using fluorescence microscopy to detect the marker tags corresponding to antigens on the reaction product. Imaging arrays, fluorescence microscopy and fluorescence spectroscopy are well known methods in the art. Thus, for instance, imaging of the checkerboard array schematically illustrated in FIG. 13B will detect Visual Label-1 (VL1) and Visual Label-3 (VL3) for the square comprising the capture probe for the oligonucleotide tag on s-1, thereby identifying Ag 1.1 and Ag 2.1 as the attributes present in the pool labeled with s-1. Similar analysis identifies the attributes in the other squares of the checkerboard. See, for instance, U.S. Pat. Nos. 6,387,707 and 6,958,245 for information regarding array cytometry.

In another embodiment, step (d) of method 50 may be carried out using microparticles. The microparticles comprise attached capture probes. As discussed above, each capture probe comprises at least one nucleotide sequence, with each nucleotide sequence being complementary to the nucleic acid sequence of a source tag. The microparticles also comprise a fluorescent label, or mixture of such labels differing in color, that identifies the capture probes attached to the microparticle. The fluorescent label may comprise an encoded fluorescence such as described in U.S. Pat. No. 7,498,054, entitled "METHOD FOR CONTROLLING SOLUTE LOADING OF POLYMER MICROPARTICLES," the entire disclosure of which is incorporated herein by reference or U.S. Pat. No. 7,083,914, entitled "Color-Encoding AND IN-SITU INTERROGATION OF MATRIX-COUPLED CHEMICAL COMPOUNDS," the entire disclosure of which is incorporated herein by reference. The source tag on an attribute-specific source tagged reaction product may be identified because the source tag anneals to a complementary capture probe on a microparticle. The microparticle fluorescent tag can be used to identify the source tag, and the fluorescent tag on the marker tag can be used to identify the attribute.

Figure 13C:
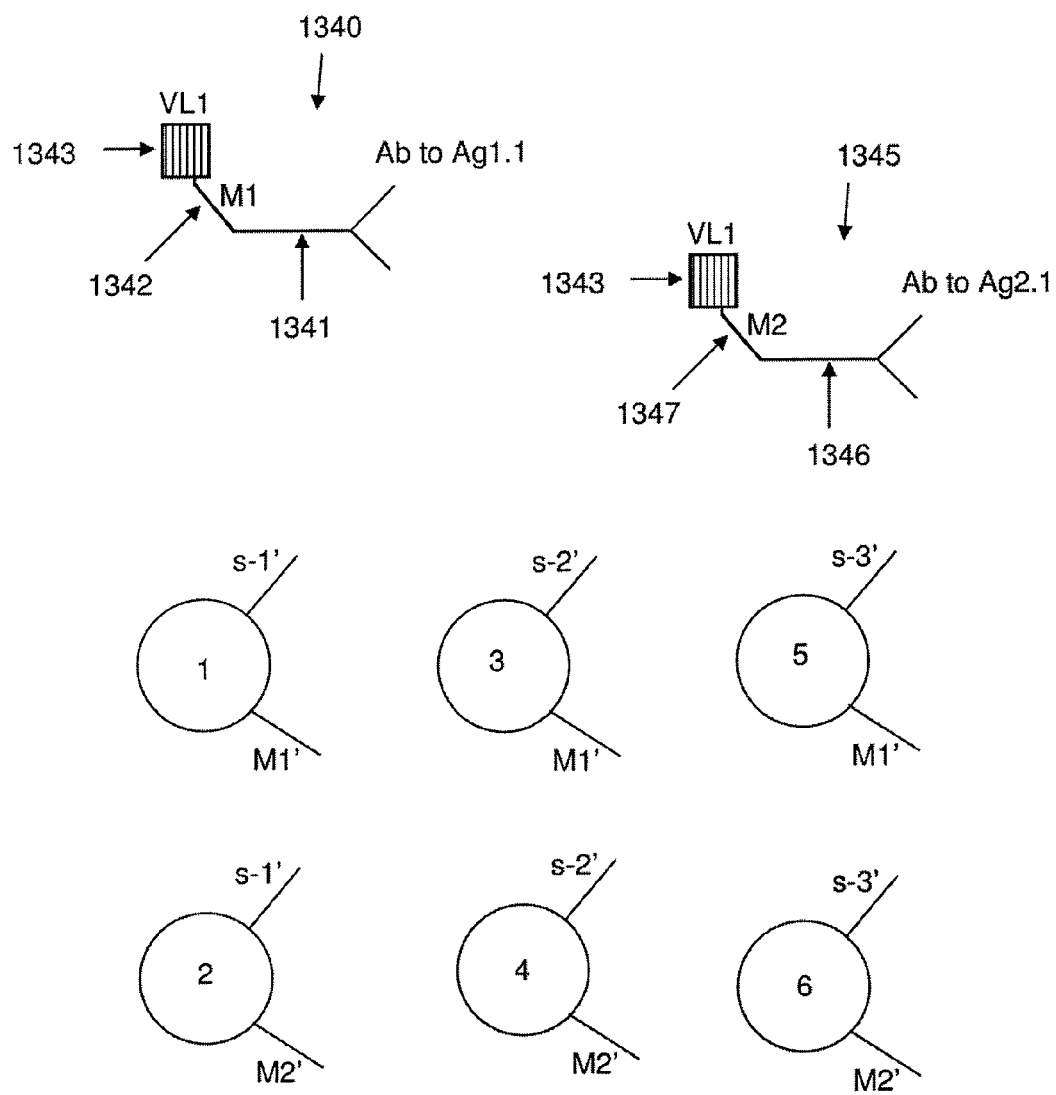
FIG. 13C schematically illustrates six (6) different microparticles used to determine antigens.

In another embodiment using microparticles, microparticles comparable in size to the reaction products, e.g., red blood cells, are prepared comprising two types of capture probes. One type of capture probe is a complement to a source tag. The other type of capture probe is a complement to a marker tag for a specific antigen. In one embodiment, the marker tag for a specific antigen comprises: a specific binding member for the antigen, an oligonucleotide tag and a visual label. The oligonucleotide tag is the same for the marker tags for each pair of antigen and antithetical antigen. The visual label will be different for the two marker tags. The top panel of FIG. 13C schematically illustrates two such marker tags. Marker tag 1340 comprises a specific binding member 1341, here an antibody to Ag 1.1, an oligonucleotide tag M1 (element 1342) and a label 1343 here designated visual label 1 (VL1). Marker tag 1345 comprises a specific binding member 1346, here an antibody to Ag 2.1, an oligonucleotide tag M2 (element 1347) and a label 1343, VL1. Microparticles are prepared for each combination of source tag and marker tag. In this example, 6 classes of microparticles are prepared, each class of microparticles comprising a fluorescent label or mixture of such labels that identifies the microparticle. The bottom panel of FIG. 13C schematically depicts the 6 classes of microparticles. S-1' is the capture probe for source tag s-1; s-2' is the capture probe for source tag s-2; and s-3' is the capture probe for source tag s-3. M1' is the capture probe for the oligonucleotide tag present in the marker tags for both Ag 1.1 and Ag 1.2. M2' is the capture probe for the oligonucleotide tag present in the marker tags for both Ag 2.1 and Ag 2.2. Attribute-specific source-tagged reaction products are contacted with the microparticles under conditions permitting hybridization of the complementary oligonucleotide sequences without destabilizing the antigen-specific binding member complexes. Hybridization of oligonucleotide sequences in the presence of antigen-specific binding member complexes is known in the art. See, for instance, Lind and Kubista. (Real-Time Immuno-PCR on the ICycler IQ™ System, Rev. A. [online], [retrieved on 2011-04-04]. Retrieved from the Internet <URL: http://www.biocompare.com/Articles/Application Note/1173/Real-Time-Immuno-PCR-On-The-ICycler-IQ-System-Rev-A.html>). Detection of the fluorescent label for a microparticle and of the label in the marker tag in attribute-specific source-tagged reaction products identifies the presence of a particular antigen on a biological sample having a particular source tag.

Figure 13D:
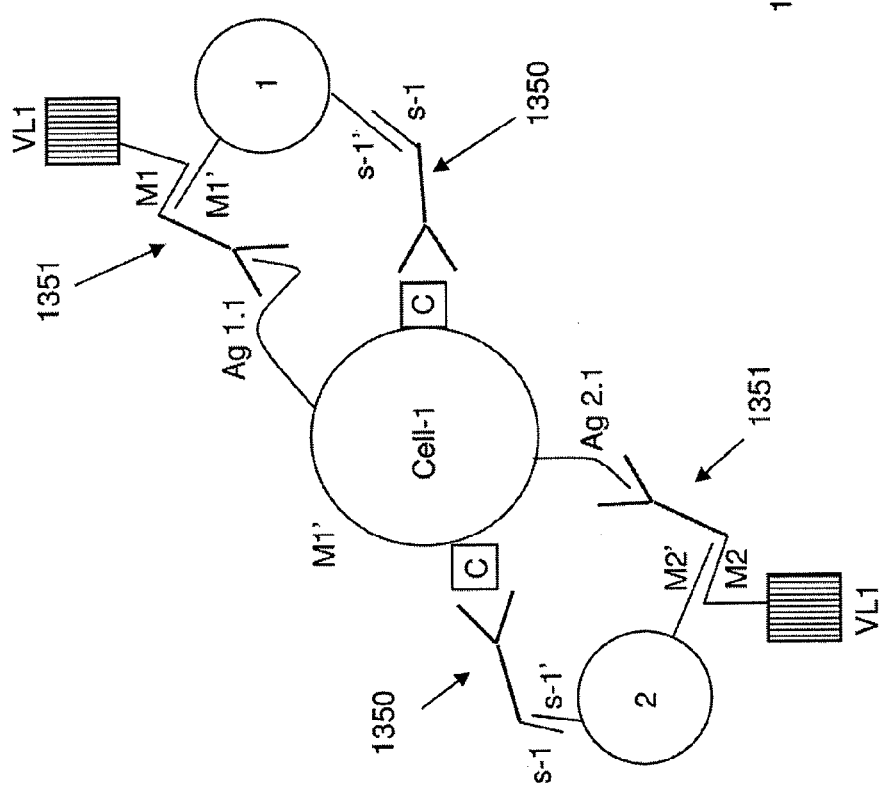
FIG. 13D schematically illustrates two different microparticles bound to a biological sample, Cell-1 and a table for identifying the source tab and antigen based on the colors detected.

FIG. 13D schematically depicts an attribute-specific source-tagged reaction product for Cell-1 in an embodiment where interrogation for both blood group Ag 1 and blood group Ag 2 occurs in the same well. Microparticle 1 comprising a capture probe for s-1 and a capture probe for M1 is bound to Cell-1. Microparticle 2 comprising a capture probe for s-1 and a capture probe for M2 is also bound to Cell-1. Detection of the fluorescent label for microparticle 1 and the fluorescent label VL1 in the marker tag identifies the source tag as s-1 and the antigen as Ag 1.1 Detection of the fluorescent label for microparticle 2 and the fluorescent label VL1 in the marker tag identifies the source tag as s-1 and the antigen as Ag 2.1. This result indicates that the attributes present on Cell-1 are Ag 1.1 and Ag 2.1. Thus, the fluorescent label for a microparticle and the label in a marker tag together encode the identity of the source tag and the specific antigen for a blood group system. Table 1360 in FIG. 13d summarizes the color combinations and what they identify for this example.

Embodiments utilizing microparticles preferably interrogate reaction products in a planar array form. In an embodiment, the microparticles are assembled ("arrayed") on a surface and are then contacted with attribute-specific source-tagged reaction products. See, for instance, Hashmi et al., "The BeadChip System: A Flexible Array Format for Complex Nucleic Acid and Protein Analysis" in BeadChip Molecular Immunohematology: Toward Routine Donor and Patient Antigen Profiling by DNA Analysis, Moulds et al. (eds.) 1$^{st}$ edition, Springer, New York, 2011, pp. 17-31.

An advantage of the microparticle having an attached capture probe complementary to a selected source tag and another capture probe complementary to a selected marker tag is that reaction products comprising both the selected source and marker tag will bind to the microparticle via the microparticle's capture probes with high affinity. The reaction products comprising both a source tag and marker tag will display higher affinity for the capture probes on a microparticle (hence "crowd out") than for reaction products which comprise only a source tag or only a marker tag.

In some embodiments, marker tags comprising oligonucleotides are interrogated by using immuno-PCR. Immuno-PCR offers the benefit of signal amplication. See, for instance, Sano et al. (1992, Science 258: 120-122) and Adler et al., (2008 Analyst 133(6):702-18. Epub 2008 Apr. 2). Indirect formats for immuno-PCR using biotin-streptavidin are also known in the art. See, e.g., WO0131056 and www(dot)i-detect(dot)eu/en_produ(dot)php.

In another embodiment, step (d) of method 50 may be carried using multi-color flow cytometry. In this embodiment, the source tag comprises a fluorescent tag in addition to the fluorescent tags of the marker tags. The attribute-specific source-tagged reaction products are then identified by identifying the fluorescent colors present in each reaction product. The fluorescent colors will identify the source and the attributes present. Multi-color flow cytometry is well known in the art and is described, for instance, in Stewart et al. (1995, Med TechNet Presentations October 23-November 12); Chattopadhyay et al. (2006, Nature Medicine 12:972-977); and Baumgarth et al. (2000, J Immunol Methods 243:77-97).

In some embodiments, the attribute-specific marker tags may not comprise visual labels. The marker tag may encode both the blood antigen group and the specific antigen present. For example, two different barcodes for the marker tag can be used, one identifying the "Normal" antigen, the other identifying the "Variant" antithetical antigen. The combination of blood antigen group and antigen code then may be detected by, for example, using microparticles comprising a source-tag capture probe, and a blood antigen group and antigen capture probe. Since there is a microparticle for each of the antigens, the antigens can be determined by identifying the microparticles (by way of their fluorescence code) bound to a cell of a biological sample.

In embodiments, some wells may be used to determine more than one blood antigen group (or set of attributes). In this case, the attribute-specific probes are designed with a marker tag that can be used to identify the blood antigen group for which the antithetical antigens are being determined. This marker tag may be designed in a number of ways. For instance, in the case of two blood antigen groups of two antigens each being determined in a single well, the visual labels of the marker tags can comprise four different colors. The marker tags in FIG. 11 are exemplary. Microparticles identify the source tag. The visual label of the marker tags identify the blood antigen group and the specific antigen.

In some embodiments, the attribute-specific source tagged reaction products are interrogated by means of anti-tags. In these embodiments, the marker tags comprise unique oligonucleotide sequences. An anti-tag can be prepared for each unique oligonucleotide sequence. In one embodiment, each anti-tag is bound to a fluorescent label. Binding of the fluorescent-labeled anti-tag to the marker tag thus renders the attribute-specific source-tagged attribute product detectable by flow cytometry or image cytometry. A visual marker is therefore not required as part of the marker tag in this embodiment.

In one embodiment, a known quantity of an anti-tag is combined with attribute-specific source-tagged reaction products under conditions that permit the annealing of the anti-tag to its complement, if present. The retention of anti-tag by the attribute-specific source-tagged reaction is thus indicative of the presence of that marker in the pooled pool of attribute-specific source-tagged reaction products. Determining if anti-tag is retained can be accomplished by determining the amount of anti-tag that is not retained, and comparing that amount of anti-tag to the amount initially added. For instance, a pooled pool of attribute-specific source-tagged reaction products can be contacted with a solution comprising a known amount of anti-tag. After allowing for annealing of the anti-tag to its complement, the solution, which contains unbound anti-tag, is eluted from, or otherwise withdrawn, from the pooled pool.

The identity and amount of anti-tag in the withdrawn solution can be assessed using methods known in the art. For instance, where the identity of the anti-tag can be assessed by its length, the withdrawn solution is subjected to a sizing assessment, such as electrophoresis (e.g., differential electrophoretic mobility) or liquid chromatography (e.g., differential elution). In a preferred embodiment, capillary electrophoresis is used for the sizing assessment. Using capillary electrophoresis, the position of each peak uniquely corresponding to one of the anti-tags (of known length), the area under the corresponding peak corresponding to the number of anti-tags of a given type. Calibration (or comparison to a reference channel) permits the quantitative determination of the decrease in concentration which is compared to a preset threshold to determine whether or not a the detected reduction in the withdrawn solution.

Figure 13E:
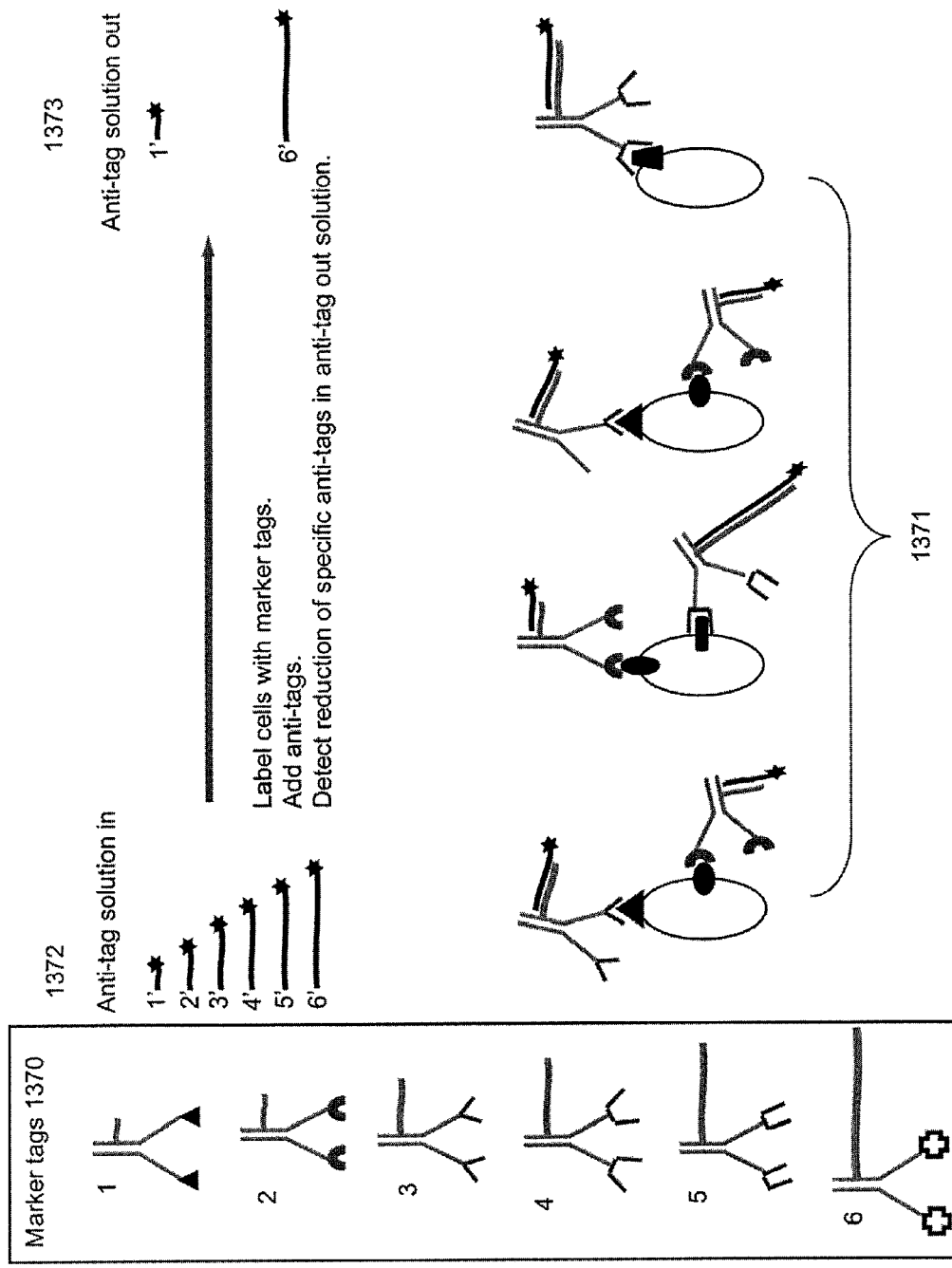
FIG. 13E schematically depicts an embodiment using a subtractive assay using anti-tags to interrogate a set of reaction products.

FIG. 13E schematically depicts the subtractive assay using anti-tags. Marker tags 1-6 (element 1370) have a specific binding member bound to an oligonucleotide tag. Each oligonucleotide tag on marker tags 1-6 is different in length. Cells are contacted with the marker tags to form reaction products. As depicted on the bottom of FIG. 13E, only marker tags 2-5 bind to the cells to form reaction products 1371. Anti-tags 1', 2', ... 6' (element 1372) which are complementary to the oligonucleotides on marker tags 1, 2, ... and 6, respectively, are combined with the reaction products under suitable hybridization conditions. The anti-tags may comprise a fluorescent label, schematically depicted as stars in FIG. 13E. Unbound anti-tags (element 1373) are withdrawn from the reaction and identified and quantified to ascertain what anti-tags were retained and in what amount.

Advantageously, this embodiment can be carried out using a plurality of different anti-tags concurrently. The number of different anti-tags that can be used concurrently is likely to greatly exceed the number of different fluorescent tags that are currently available. It is therefore expected that use of the anti-tag subtractive assay to interrogate attribute-specific source-tagged reaction products can further contribute to the extent of multiplexing over that provided by fluorescent colors.

To interrogate attribute-specific source-tagged reaction products regarding the source tags associated with the retained anti-tags, checkerboard arrays comprising capture probes for the source tags may be used. In this embodiment, the anti-tags comprise a fluorescent label.

In another embodiment, anti-tags may comprise both an anti-tag to a marker tag (i.e., specific attribute) and a source tag oligonucleotide tag. This construct permits simultaneous determination of what source tag (e.g., which pool) comprises the biological sample expressing the attribute. To relieve possible spatial constraints associated with annealing to both an oligonucleotide tag of a marker tag and an oligonucleotide tag of a source tag, the anti-tag to the marker tag may be separated from the anti-tag to the source tag by a spacer molecule, which may be an oligonucleotide or other moiety.

In some embodiments, molecular beacons designed to detect designated source tag and marker tag combinations on reaction products may be used. The beacons may be color-coded to distinguish individual species of beacon.

In some embodiments, capture probes complementary to source tags and/or marker tags are provided on separate spectrally distinguishable nanoparticles so that two nanoparticles will attach to the reaction products containing the target source tag and maker tag. Because of the specific combination of source tag and marker tag, there will be a specific dual-color signature that may be used to identify the source tag and marker tag (see, for instance, manufacturing instructions for use of Qdot™ Nanocrystals, Invitrogen, Carlsbad, Calif.).

Figure 13F:
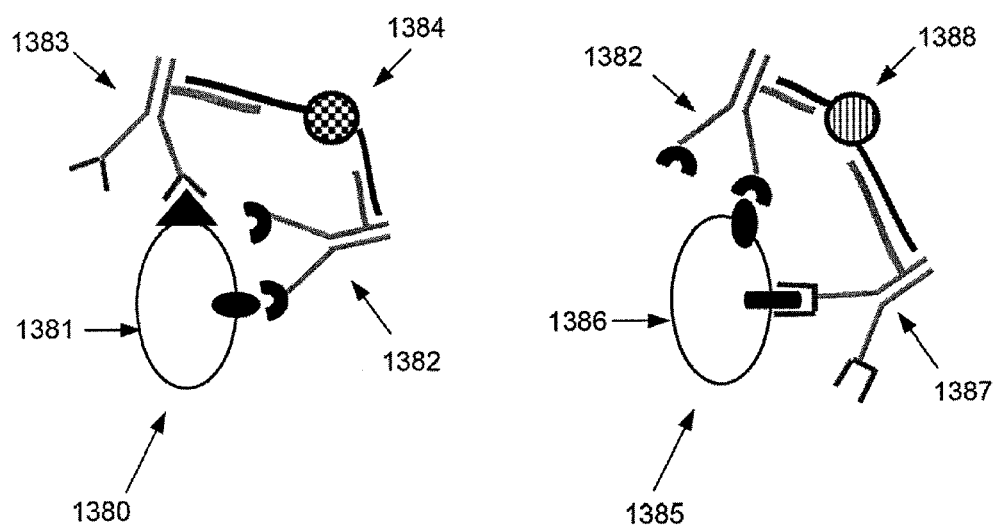
FIG. 13F schematically illustrate two different nanoparticles bound to a biological sample.

In some embodiments, capture probes complementary to a source tag and a marker tag are provided on the same nanoparticle. The nanoparticles permit single-wavelength excitation to produce 5-7 or so (depending on the particle size) emission wavelengths. A schematic depiction of this embodiment is shown in FIG. 13F. Reaction product 1380 comprises cell 1381 to which is bound source tag 1382 and marker tag 1383. Nanoparticle 1384 is bound to the oligonucleotide tags on source tag 1382 and marker tag 1383. Detection of the color of the nanoparticle thus identifies both the source tag and the marker tag. If the oligonucleotide tag on the marker tag identifies a specific antigen (e.g., variant), then the color of the nanoparticle also identifies the specific antigen. Also in FIG. 13F, reaction product 1385 comprises cell 1386 to which is bound source tag 1382 and marker tag 1387. Nanoparticle 1388 is bound to the oligonucleotide tags on source tag 1382 and marker tab 1387. Nanoparticle 1388 has a different color than nanoparticle 1384. Thus, detection of the color of nanoparticle 1388 thus identifies both the source tag 1382 and the marker tag 1387. If the oligonucleotide tag on the marker tag identifies a specific antigen (e.g., variant), then the color of the nanoparticle also identifies the specific antigen.

Embodiments utilizing nanoparticles preferably interrogate reaction products in a fluid form, for instance, a suspension of cells. For instance, nanoparticles comprising combinations of a source tag capture probe and a marker tag capture probe may be added to a suspension of attribute-specific source tagged attributes. The suspension is illuminated at an excitation wavelength and the resulting emission wavelengths are detected. In an embodiment, the process may be practiced using flow cytometry.

Thus, in the embodiment illustrated above, the attribute profile of Cell-1, Cell-2 and Cell-3 can be determined for blood group 1 and 2.

Identifying Blood Group Antigens of Red Blood Cells ("d"=1; One Blood Group Antigen)

The International Society of Blood Transfusion (ISBT) currently recognizes 30 major blood group systems (including the ABO and Rh systems). The ISBT definition of a blood group system is where one or more antigens are controlled at a single gene locus or by two or more very closely linked homologous genes with little or no observable recombination between them. FIG. 14A illustrates a table of seventeen blood group systems having antithetical antigens. The names of the antithetical antigens is shown in the "Antigens" column. The antithetical antigens result from DNA polymorphisms, as shown in the Polymorphism column.

Figure 14B:
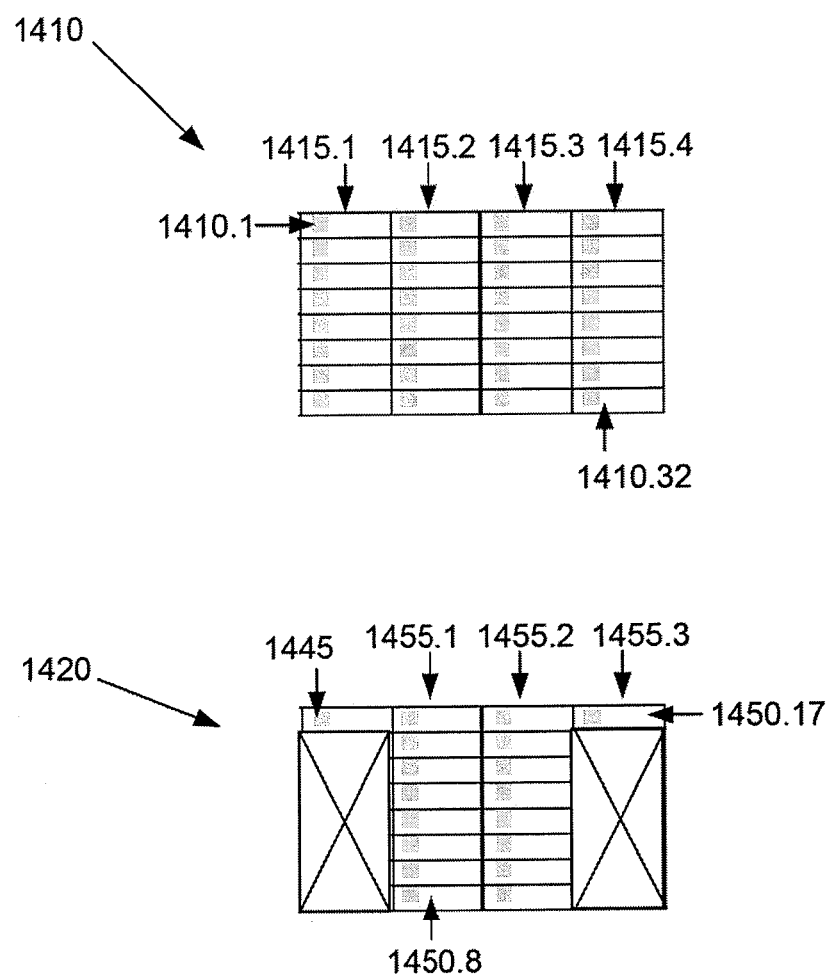
FIG. 14B schematically illustrates in part an embodiment of the method of FIG. 3 that determines the attribute profile for the seventeen (17) blood groups listed in the table in FIG. 14A for thirty-two (32) blood samples, where in this example the antigens for only one blood group are determined at a time.

FIG. 14B illustrates the operation of an embodiment of method 50 illustrated in FIG. 3 of identifying attributes of a plurality of blood groups (17 as listed in the table in FIG. 14A) in a plurality of biological samples (32 are used in this example). In this embodiment, the biological sample is a blood sample comprising red blood cells. The difference between the embodiment illustrated in FIG. 14B and the previous embodiment illustrated in FIGS. 3-7 is that in FIG. 14B, the attributes of only one blood group are determined per pool.

The method 50 of FIG. 3 (as now applied to identification of antigens of a plurality of blood groups) begins with step (a): for each of the antigens to be identified, determining a source tag sharing number "d" for the allele. All the polymorphisms are determined to have a source tag sharing number "d"=1. The application of the method of allele determination with source tag sharing numbers other than 1 is discussed later in this specification.

The method 50 of FIG. 3 (as now applied to identification of antigens of a plurality of blood groups) continues with step 120 (*b*): for each of the different determined source tag sharing numbers "d": (i) dividing the plurality of biological samples into biological sample subsets. Each subset contains approximately the source tag sharing number "d" of biological samples, so that each biological sample of the plurality of biological samples is included in at least one subset. Here, as discussed above, for this example of the method 50 the source tag sharing number "d" is equal to 1 is used for all 17 blood groups illustrated in FIG. 14A.

Step 120 (*b*) continues with (ii): for each of the biological sample subsets, placing a portion of each of the biological samples included in the sample subset into a pool. This thereby provides a plurality of pools for the source tag sharing number "d" with each pool comprising a pooled subset of biological samples.

The following is an example of the performance of step 120 (*b*) (i) and (ii) of method 50 in FIG. 3 (as now applied to identification of antigens of a plurality of blood groups).

Depicted in FIG. 14B is plate 1410 (or microtiter plate) which is a general purpose laboratory consumable that often contains ninety-six (96) (8 rows by 12 columns) wells 1410.1, 1410.2 . . . 1410.96 and may be used to perform experiments with samples that comprise biological samples. Note that, for convenience, only thirty-two (32) of the ninety-six (96) wells are illustrated as plate 1410. As discussed above, for step 120 (*b*) (i) there is one biological sample per subset. And, for step 220 (*b*) (ii) each of the thirty-two (32) biological samples is placed in one of the wells 1410.1, 1410.2 . . . 1410.32 of columns 1415.1, 1415.2, 1415.3, and 1415.4 of plate 1410. It will be appreciated that the wells comprise "pools" as defined herein.

Method 50 of FIG. 3 continues with step 210 (*c*): for each pool of the plurality of pools for the source tag sharing number "d," produce at least one pooled pool comprising attribute-specific source-tagged reaction products from at least two pools of the plurality of pools for each of the different determined source tag sharing numbers "d," wherein the attribute-specific source-tagged reaction products comprise biological samples comprising a source tag identifying said each pool and a marker tag that uniquely identifies an attribute. One embodiment of step 210 (*c*) in FIG. 3 is illustrated in FIG. 4 as step 210.1 (*c*), which comprises (i): for each pool of the plurality of pools for the source tag sharing number "d", performing a reaction (in this example a binding reaction) in the pool (in this example, contained in wells of a microtiter plate) to produce source-tagged reaction products (in this example red blood cells to which the source tag is bound) wherein the source tag identifies said each pool (in this example source tags with oligonucleotide barcodes).

The following is an example of how step 210.1 (*c*) (i) may be performed. Source tags are added to each well. The source tags comprise a specific binding member that binds to a common antigen on the red bloods and an oligonucleotide barcode. For instance, the specific binding member could be an aptamer that binds phospholipid or an antibody, such as an anti-phospholipid Fv, Fab or $F(ab)_2$. In this example, the specific binding member is an anti-phospholipid antibody (in this example Ab-c). The antibody Ab-c is bound to a source tag (s-1, s-2, . . . s-32) for identifying the well into which it has been placed, 1410.1, . . . , 1410.32. The thirty-two source tags comprise barcodes. The thirty-two red blood cell samples in the wells are bound with antibody comprising the source tag (barcode), thereby producing source-tagged reaction products: $^{s-1}$reaction product, $^{s-2}$reaction product, . . . $^{s-32}$reaction product.

The method 50 of FIG. 3 continues with step 210.1 (*c*) (ii): pooling in at least one pooled pool at least some of the said produced source-tagged reaction products from at least two pools of the plurality of pools for the source tag sharing number "d." This provides a plurality of pooled pools comprising at least one pooled pool for each of the different determined source tag sharing numbers "d." In the present example, "d"=1. Therefore, the red blood cell samples each have their own source tag which can be used to identify not only the pool from which they came but also the red blood cell sample.

The following is an example of performing step 210.1 (*c*) (ii) of FIG. 4. Aliquots from all of the thirty-two (32) wells 1410.1, . . . , 1410.32 are placed into well 1445 of new plate 1420. Note that as illustrated in FIG. 14B, separate plates 1410 and 1420 are used, but the same plate could be used. Aliquots are then taken from well 1445 and placed into seventeen (17) new wells, 1450.1 through 1450.17 so that each of wells 1450.1 through 1450.17 contains source-tagged red blood cells from each of the thirty-two (32) biological samples $^{S-1}$reaction product, $^{S-2}$reaction product, . . . $^{S-32}$reaction product. Notice that only three columns, 1455.1, 1455.2, and 1455.3, are needed to accommodate these 17 new pools, which is the number of blood groups to be determined.

The method 50 of FIG. 3 continues with step 210.1 (*c*) (ii): for each of the attribute to be identified, performing a second reaction (in this examples, a binding reaction) using said source-tagged reaction products (red blood cells bound with a specific binding member which further comprises a barcode) to produce attribute-specific source-tagged reaction products comprising a marker tag (in this example a specific binding member that binds to the attribute and comprising a visual label). The marker tag uniquely identifies an attribute, and wherein the second reaction is in the pooled pool for the source tag sharing number "d", the "d" corresponding to the source tag sharing number "d" determined for the attribute in step (a). In this example, the source tag sharing number "d" is 1 for all the attributes.

The following is an example of step 210.1 (*c*) (ii) of FIG. 4. The attributes at only one blood group are determined per well 1450. Referring to FIG. 14B, two types of attribute-specific tags are added to each well 1450.1, 1450.2 . . . 1450.17. One attribute specific tag comprises a specific binding member for one antigen (e.g., normal) of the blood group being assessed in the well. A second attribute specific tag comprise a specific binding member for the other antigen (e.g., variant) of the blood group being assessed in the well.

For example, in well 1450.1 of FIG. 14B, the antigen for the blood group MNS (see FIG. 14A) is assessed. A specific binding member for antigen M, Ab-M, is designed to bind to source-tagged reaction product that has the M antigen displayed on the cell surface. A specific binding member for antigen N is designed to bind to source-tagged reaction product that has the M antigen displayed on the cell surface. Each specific binding member is bound to a visual label to form an attribute-specific marker tag. Thus Ab-M is bound to visual label 1 to form marker tag $M^{VL1}$ and Ab-N is bound to visual label 2 to form marker tag $N^{VL2}$. In this example, visual label-1 is a fluorescent green, and visual label-2 is a fluorescent red.

For the 17 wells that are illustrated in FIG. 14B, 17 different versions of the marker tags comprising visual label 1 are designed, each having a specific binding member specific to one of the antigens (e.g., normal) in the blood group to be assessed. Seventeen (17) different versions of the marker tags comprising visual label 2 are designed, each version having a specific binding member to the other of the antigens (e.g., variant) in the blood group to be assessed.

The marker tags, marker tag$^{VL1}$ and marker tag$^{VL2}$ designed for each well, are added to the respective wells, 1450.1, . . . , 1450.17. In each well, because of the design of marker tag$^{VL1}$, attribute-specific source tagged reaction products comprising marker tag$^{VL1}$ will be produced if the red blood cells display the cell surface antigen to which the specific binding member of marker tag$^{VL1}$ binds. The produced attribute specific source-tagged reaction product will be of the form, $^{S-N}$reaction product$^{VL1}$. Similarly, because of the design of marker tag$^{VL2}$, attribute-specific source-tagged reaction products comprising marker tag$^{VL2}$ will be produced if the red blood cells display the cell surface antigen to which the specific binding member of marker tag$^{VL2}$ binds. The produced attribute specific source-tagged reaction product will be of the form, $^{S-N}$reaction product$^{VL2}$.

Alternative methods may be used where the antigen is identified by the length of the marker tag rather than using a visual label as the marker tag. Alternatively, beacons may be used to indicate the antigen.

The method 50 of FIG. 3 continues with step 220 (*d*): identifying said attribute-specific source-tagged reaction products by interrogating said reaction products comprising said source tag and said marker tag. If the interrogating of the attribute-specific source-tagged reaction products indicates unambiguous results, then the antigen is identified. Otherwise, if the interrogating of the source tag and the marker tag of the reaction products indicates ambiguous results, then disambiguating the ambiguous results is required.

The following is an example of performing step 220 (*d*) of FIG. 3. The fluorescent colors present in each well comprising attribute-specific source tagged reactions products 1450.1, 1450.2 . . . 1450.17 (FIG. 14B) are assessed, for instance, by flow cytometry. If a single fluorescent color detected for a well, such as fluorescent green (visual label-1), the attribute is unambiguously identified for each of the 32 different biological samples in the well. If two fluorescent colors are detected, e.g., both fluorescent green and fluorescent red (visual label-2), the results are ambiguous and may need to be disambiguated. In this example, since each biological sample bears its own source tag, assessing the source tag identity in combination with the marker tag information may disambiguate the results.

In an embodiment, thirty-two different types microparticles are prepared, each type comprising a capture probe complementary to one of the thirty-two source tags on the reaction products: $^{S-1}$reaction products, . . . , $^{S-32}$reaction products. The microparticle capture probe thud determines which of the biological samples may anneal to the microparticle. The microparticles comprise visual identifiers that can be decoded to determine the identity of the microparticle. In one embodiment, the visual code comprises six different fluorescent entities (such as "nanoparticles") to encode the identity of a microparticle (and the capture probe attached to it). The microparticles may comprise a binary tag arising from the six different fluorescent colors. The thirty-two different types of microparticles are added to each of the wells 1450.1 to 1450.17 illustrated in FIG. 14B. Thus, each of the wells 1450.1 to 1450.17 contain microparticles 1 to 32. The wells 1450.1 to 1450.17 are then examined to determine the source tag identity and the marker tag identity. In some embodiments, a portion of the attribute-specific source-tagged reaction products from each well 1450.1 to 1450.17 can be placed in contact with a pre-assembled array of the microparticles, or with a suspension of the microparticles.

In an embodiment, a portion of the attribute-specific source-tagged reaction products in a well can be contacted with a nucleic acid array, such as a checkerboard array. The identity of the source tag is encoded by the physical location on the checkerboard. The array is the imaged to detect the fluorescent colors present in each physical location, thereby identifying the antigens based on the marker tags.

In embodiments, some wells may be used to determine more than one blood group. In this case, the antigen-specific marker tags are designed such that different antigens of the blood groups can be identified.

The example above illustrates a number of advantages of embodiments of the invention over existing methods of attribute determination. In some existing methods, an attribute profile is determined for one sample at a time. In one such prior method, one biological sample without a source label is contacted with marker tags for different antigens. The sample is then analyzed by fluorescence-activated cell sorting (FACS; also referred to as flow cytometry). Applying this existing method may take five to six hours for a complete attribute determination of the seventeen blood groups in FIG. 14A for a single sample. The time and cost increases proportionally if a plurality of samples must be analyzed. The method described with reference to FIG. 14B has the advantage of a higher rate of producing attribute determinations than the existing method of analyzing a single sample. The advantages of the method with regard to allele profiling are described in detail in commonly-assigned, co-pending application "METHOD FOR DETERMINING AN ALLELE PROFILE OF NUCLEIC ACID," filed on even date herewith, incorporated herein in its entirety by reference. FIG. 9 therein illustrates the difference in some embodiments of allele profiling using a binning and group testing method of the invention and a traditional method of determining an allele profile for thirty-two nucleic acid samples and twenty polymorphic sites. The advantages of the method of the invention illustrated therein are also achieved when attribute profiling a plurality of biological samples.

Ambiguities and Disambiguation

The example of the operation of the invention illustrated with FIG. 8 deals with the source tag sharing number "d"=1. The value of "d" will determine the number of biological samples that share a source tag. Source tag sharing numbers "d">1 can be advantageous when the frequency of an antigen is low. For example, the Colton 760 blood group system illustrated in the table in FIG. 14A comprises two alleles encoding two antigens: one of the alleles (which encodes antigen $Co^a$; "normal") occurs with over 99% probability (probabilities not illustrated in table) and the other allele (which encodes antithetical antigen $Co^b$; "variant") occurs with less than 1% probability (in Caucasians). By using the same source tag for more than one biological sample, the number of operations in determining antigen profiles for a given number of biological samples may be reduced (compared with the conventional "one-sample-at-a-time" method). However, if all of the antigens are not the how an ambiguity may arise when biological same for a blood group for all the biological samples sharing the same source tag code, then the methods disclosed above may not unambiguously identify the antigens in step (d) of the method 50 without additional disambiguation as described below.

Figure 15:
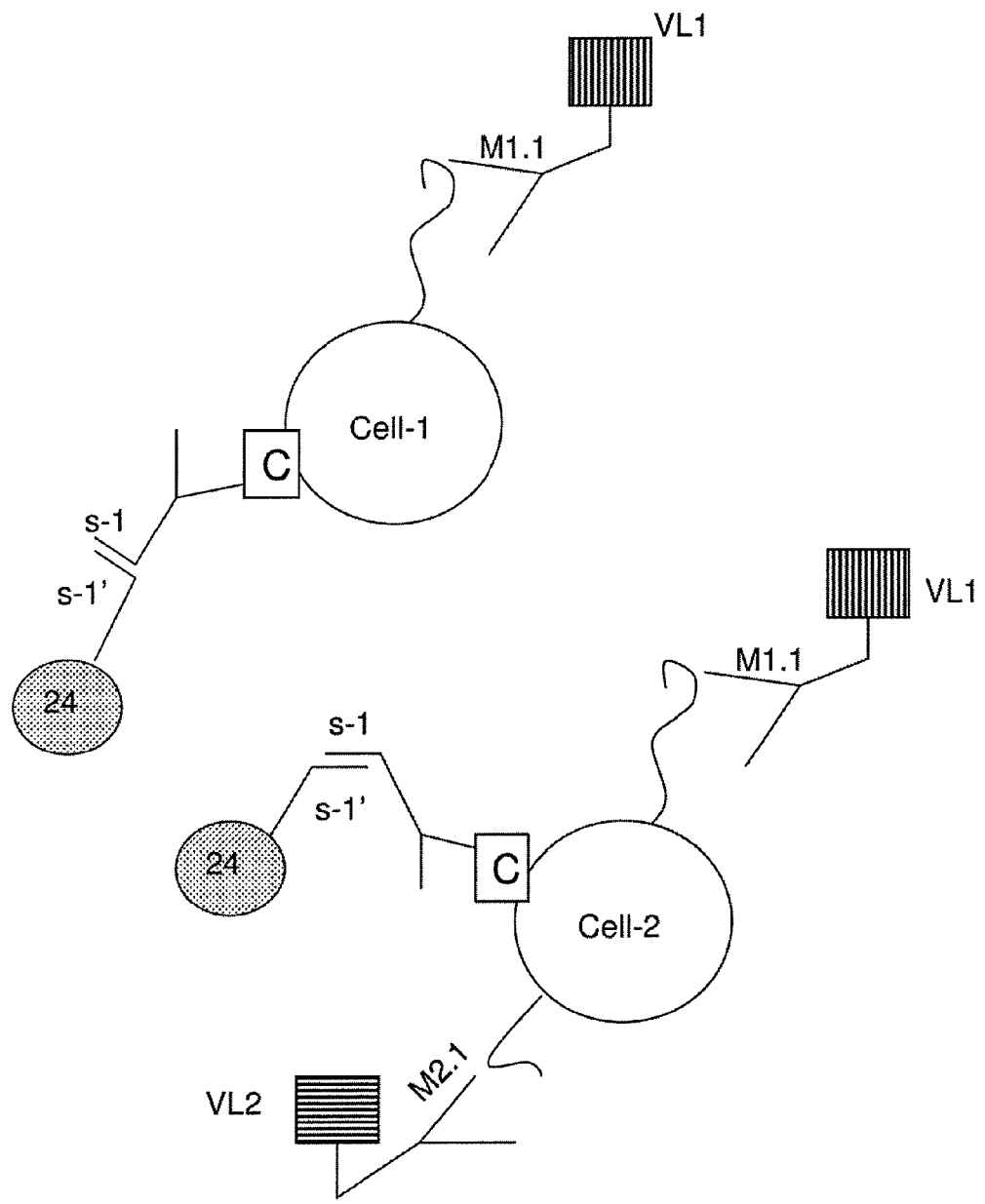
FIG. 15 schematically illustrates two cells sharing source tag s-1 and bound to marker tags for antigen $Co^a$ (M1.1=VL1) and antigen $Co^b$ (M1.2=VL2)

FIG. 15 illustrates samples share source tags, in the case where the alleles encoding the antigens are both expressed when present (e.g., co-dominant alleles). Illustrated in FIG. 15 are two attribute-specific source-tagged reaction products produced from Cell-1 and Cell-2. As shown in FIG. 15, Cell-1 only expresses $Co^a$ on its surface (and is therefore homozygous for the allele encoding antigen $Co^a$). The marker tag for this antigen, comprising a specific binding member (M1.1) for $Co^a$ and visual label-1, is bound to Cell-1. Cell-2 expresses both $Co^a$ and $Co^b$ on its surface and it is therefore heterozygous. Cell-2 is therefore bound by a marker tag for $Co^a$ and a marker tag for $Co^b$. The marker tag for $Co^b$ comprises a specific binding member (M1.2) for Co and visual label-2. Cell-1 and Cell-2 are pooled, and the same source tag s-1 is added to the pool.

As illustrated in FIG. 15, the signal that is recorded from a microparticle 24 having a capture probe that anneals to source tag s-1 would indicate the presence of both visual label VL-1 and visual label VL-2 in the pooled pool. The detection of both visual labels indicates at least one biological sample having source tag s-1 is heterozygous, or homozygous for the variant (e.g., $Co^b$), for this blood group. If the method of identifying the antigen is quantitative, it may be possible to distinguish whether Cell-1 is heterozygous or homozygous.

FIG. 16A illustrates the visual labels that would be present for combinations of Cell-1 and Cell-2 having different phenotypes, wherein heterozygotes express both alleles (i.e., codominant alleles) or when testing a collection of non-allelic antigens, where two antigens may both be expressed. Along one axis are the three possible phenotypes for Cell-1 and along the other axis are the three possible phenotypes for Cell-2. "A" represents one antigen and "a" represents the antithetical antigen. The signal is unambiguous only if both Cell-1 and Cell-2 are homozygous for the same allele, and thus express the same, sole antigen. For instance, if both Cell-1 and Cell-2 express only antigen "A," then the only visual label-1 will be detected. Based on the frequency of a given allele in a population, one can calculate the probability of both cells being homozygous for "A." For example, let the allele encoding antigen "A" have a frequency of 90%, that is f(A)=0.9; and the allele encoding antigen "a" have a frequency of 10%, that is f(a)=0.1. The probability that Cell-1 is homozygous for A is therefore 0.9*0.9=0.81. The probability that Cell-2 is homozygous for the allele encoding "A" is also 0.81. The probability that in a pool of two biological samples, Cell-1 and Cell-2, are both homozygous for "A" (i.e., AA) is therefore 0.81*0.81=0.6561; thus, the equation for this probability is $p(A)^4$. The probability of a configuration in which only visual label-1 is detected is 0.6561 or almost ⅔ of the time. See FIG. 16B. The other entry in the illustration in FIG. 16A for which there is no ambiguity is where both Cell-1 and Cell-2 are homozygous for the allele encoding antithetical antigen "a." The probability that Cell-1 is homozygous for the allele encoding antigen "a" is 0.1*0.1=0.01; thus, the equation for this probability is $p(a)^4$. The probability that in a pool of two biological samples, Cell-1 and Cell-2, are both homozygous for antigen "a" (i.e., aa) is therefore 0.01*0.01=0.0001. Hence the probability of no ambiguity for this configuration is 0.0001. The probability for an ambiguity (Prob(ambiguity)) is equal to 1 minus the probability of an unambiguous result. In this example then: Prob(ambiguity) =1−(0.6561+0.0001)=0.3438. This is the probability that the colors detected will include both VL1 and VL2. See the gray region in FIG. 16B.

In the case where heterozygotes do not express both alleles (i.e., dominant/recessive alleles) or, for non-allelic antigens, where both antigens are not expressed simultaneously, the probability of ambiguity is reduced to that of encountering a homozygous variant in a pool comprising two or more biological samples.

Often the antigen that has the highest probability of occurring for a set of antigens, such as a blood group, is referred to as the normal (N) antigen and the antigen that has the lower probability of occurring is referred to as the variant (V) antigen. The variant antigen also may be referred to as "mutant" and the normal antigen as "wild-type," especially for antigens known to be associated with disease.

For two biological samples sharing a source tag, the probability of an ambiguity occurring is given by Equation (1):

$$\text{Probability(ambiguity)} = 1 - f(N)^4 - f(V)^4 \qquad (1)$$

As discussed above for FIG. 16B, Prob(ambiguity)=1−(0.9)⁴−(0.1)⁴=−0.6561−0.0001=0.3438. Similarly, the binomial theorem can be used to determine the probability of an ambiguity, for four biological samples sharing the same source tag. Accordingly, let "d" be equal to the number of biological samples sharing the same source tag. In this case, d=4. For a set of antigens having two possible antigens, the probability of ambiguity is given by: Prob(ambiguity)=1−f(n)$^{d*2}$−f(v)$^{d*2}$, or 1−f(N)⁸−f(V)⁸. The greater the number, "d", of biological samples sharing the same source tag, the greater the chance of an ambiguity. The less frequent the variant antigen, the lower the probability of an ambiguity for a given value of source tag sharing number "d". In general, the probability of an ambiguity for a set of antigens with m possible antigens is given by Equation (2):

$$\text{Probability(ambiguity)} = 1 - f(N)^{m*d} - f(V)^{m*d} \qquad (2)$$

where as above, f(N) is the frequency of a normal antigen, f(V) is the frequency of a variant antigen, and "d" is the number of samples sharing the same source tag.

Equation (2) can be used to determine a source tag sharing number, "d," to use to determine an antigen for a set of antigens, such as a blood group. If the "Probability (ambiguity)" is set to a particular value, then all the terms in Equation (2) are known except the value of "d," which can be solved for.

The "Probability (ambiguity)" may be set to the highest acceptable probability of an ambiguity occurring in a set of "d" nucleic acid samples sharing the same source tag. This highest acceptable possibility of ambiguity may be denoted "C". Given a value of "C", a value of "d" may be determined from Equation 2.

The highest acceptable possibility of ambiguity, "C," may be determined prior to determining the source tag sharing numbers. Alternatively, source tag sharing numbers may be determined for different values of "C" to determine a set of source tag sharing numbers that will produce more efficient antigen determination. Some antigens may be identified in the same pools as other antigens. In this case, the antigens may be said to be binned in that the antigens will be determined with the same source tag sharing number. In some embodiments, antigens may be binned and different source tag sharing numbers may be used to determine different antigens.

The value of "d" may be set to the largest integer of the form 2^n (some of the more common numbers used for this method of 2^n are n=1, 2^1=2; n=2, 2^2=4; n=3, 2^3=8; n=4, 2^4=16; n=5, 2^5=32; n=6, 2^6=64; and, n=7, 2^7=128) so that the value of Equation 2, "Probability (ambiguity)" is less than "C." The value of "d" may also be limited by a preset maximum pool size (e.g. 32), which may be related to technical reasons that limit the pool size.

In the method 50 of FIG. 3, the value "C" represents the probability that the attribute determination for a plurality of biological samples is ambiguous (typically caused by at least one constituent sample displaying both antigens) and thus that additional steps are needed to resolve the ambiguity. The source tag sharing number, "d", of method 50 may be determined from Equation (2) for the largest "d" so that Probability (ambiguity) is less than C. Accordingly, Equation (3) can be used to determine the maximum number of "d" given C and the frequency of the variant allele, f(V):

$$d = 0.5 * \log(1-C)/\log(1-f(V)) \qquad (3)$$

Preferably, as in FIG. 17A, "d" is set to the largest integer of form 2^n that is less than or equal to the value "d" produced by Equation (3) for a preset "C".

FIG. 17A illustrates another example of the method 50 of FIG. 3 applied to identifying antigens of a plurality of blood groups in a plurality of biological samples. In this example, source tag sharing numbers "d" are determined for more than just the case where "d"=1, as in the previous examples of the method 50. Note that "Hemoglobin S" is not a blood group, but rather the polymorphism associated with sickle cell disease. The invention may also be used for the identification of such attributes.

An example of step (a) of method 50 of FIG. 3 of determining a source tag sharing number "d" for the allele for each of the antigens to be identified is described with reference to FIG. 17A. Table 1710 illustrates an arrangement of blood group systems 1750 and their allele frequencies observed in African Americans and in Caucasians (columns 1756 and 1758 in tables 1710 and 1730, respectively). The features of table 1710 include ISBT designation (element 1752); polymorphic site name (element 1754); the frequency of allele A (encoding antigen A) (element 1756); and, the frequency of allele B (encoding antithetical antigen B) (element 1758). The frequencies of the alleles are sometimes approximated with a "1" or "0".

Two values are set prior to determining the source tag sharing number "d". Referring to FIG. 17A, these values are: "C" (element 1770) and maximum pool size, "Max PoolSz" (element 1772). "C" (element 1770), as discussed above, is the highest acceptable probability of an ambiguity occurring in a plurality of "d" biological samples. The "Max PoolSz" (element 1772) may be determined by limitations arising from the steps of the method. For example, in some embodiments, two microparticles with different tags are added to a pool to identify antigens of a single biological sample. Thus, the number of biological samples that are pooled together is limited by the number of different microparticle tags that can be manufactured. In this example, "C" (element 1770) is set at 18% and "Max PoolSz" (element 1772) is set at 32.

The minimum frequency of the allele with the lowest frequency is represented as "f" (element 1760). A "d(S)" (element 1762) is calculated using Equation (3) with C=0.1800 (element 1770). The logarithm to the base 2 (element 1764) is calculated for each of the "d(S)" values (element 1762) and rounded down to the nearest whole integer. The number "2" is then raised to the logarithm to the base 2 (element 1764) which yields the number of samples "d" to use for the source tag sharing number of method 50 (element 1766) where "d" is of the form 2^n for n an integer such that Equation (2) "Probability (ambiguity)" is less than C (18%) (element 1770). The "power of 2" value in element 1766 is reduced to the "Max PoolSz" (element 1772), when necessary. For example, the calculated "d(S)" (element 1762) for allele "CO" (element 1754) is 99.1758, and the closest "power of 2" less than 99.1758 is 64. But since 64 is greater the "Max PoolSz" (element 1372) of 32, then "Max PoolSz" is used for the source tag sharing number "d" of method 50.

Table 1720 in FIG. 17A illustrates the alleles from table 1710 binned into the source tag sharing "d" number, which is the number of source samples that may share the same source tag. For example, the allele for blood group system Scianna, "SC" (element 1754), is placed into a bin with a source tag sharing number "d"=32 because its value for "d," shown in element 1766 is 32. The number of bins illustrated in table 1720 is 6, for "d" of 1, 2, 4, 8, 16, and 32, which is all the bins that are possible for powers of 2 that do not exceed 32. The total number of attributes (element 1776) is listed for each of the bins. Attributes that have the same source tag sharing number "d" may be identified in the same pool. Attributes that are identified in the same pool may be said to be binned together.

Similarly, tables 1730 and 1740 of FIG. 17A illustrate the source tag sharing numbers "d" and attribute binning of the blood groups systems for Caucasians. Note the difference in the frequencies of the alleles encoding the antigen and antithetical antigen (1756 and 1758) between the two groups. For example, the variant form of "SC" (1754) has a frequency of 0.006 in Caucasians and only 0.002 in African Americans, which results in "SC" being in the 32 bin for African Americans, but in the 16 bin for Caucasians.

FIGS. 12 and 13 and related description in commonly-assigned, co-pending application "METHOD FOR DETERMINING AN ALLELE PROFILE OF NUCLEIC ACID," filed on even date herewith, illustrate the method for determining the allelic profile of 384 different blood samples for the 16 polymorphic sites illustrated in FIG. 12 therein (corresponding to FIG. 17A in the present application). The description in the co-pending application is exemplary for identifying attributes of a plurality of biological samples.

The method 50 of the present invention includes the step of disambiguating ambiguous results, if interrogation of the attribute-specific source-tagged reaction products indicate ambiguous results. In some embodiments, the method 50 is repeated for the attribute for which an ambiguous result is indicated. The method 50 is repeated with the source tag sharing number "d" reduced so that the number of biological samples in pools sharing a source tag is reduced. For example, if the method 50 is performed with the source tag sharing number "d"=8, and an ambiguity is detected at an antigen for the 8 biological samples sharing a source tag, then the method may be performed with the 8 biological samples with a source tag sharing number less than 8, for example d="1". Performing the method with the source tag sharing number d="1" for the eight biological samples for determining the antigen for a particular blood group, would mean that none of the biological samples would share a source tag so there would be no ambiguities and the method would determine the antigen for the particular blood group for each of the 8 biological samples.

In some embodiments, if there is an ambiguity in determining an antigen for the particular blood group for a group of biological samples, the source tag sharing number "d" may first be reduced to a lower source tag sharing number and the method performed with the lower source tag sharing number. If there is still an ambiguity, the method may be performed again with an even lower source tag sharing number. These steps may be repeated until the source tag sharing number "d" is reduced to 1, in which case there will be no ambiguities because biological samples do not share a source tag with a source tag sharing number "d"=1.

Figure 17B:
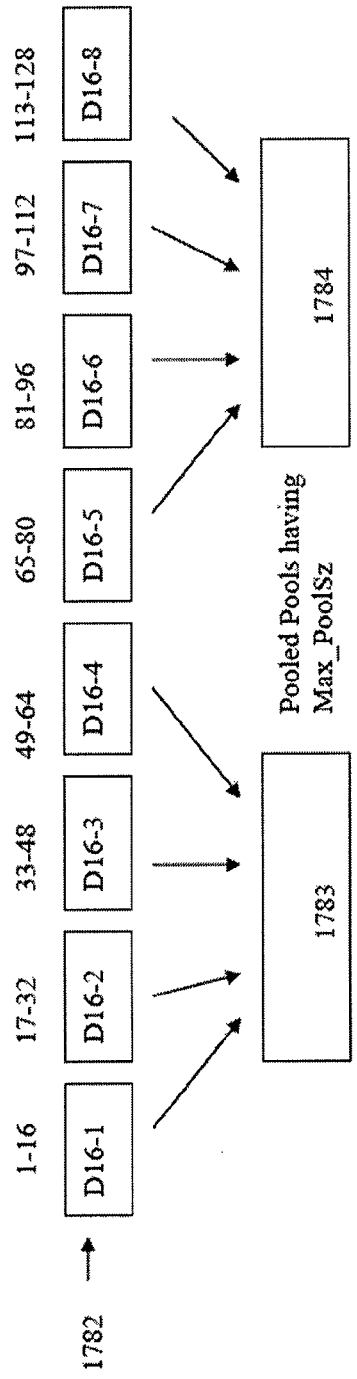
FIG. 17B schematically illustrates an embodiment of disambiguation.

In some embodiments, other antigens to be identified may be identified with the antigens that were not identified unambiguously. FIG. 17B illustrates such an embodiment. For this embodiment, the plurality of samples equals 128. "Max PoolSz" is set to 64. The source tag sharing number "d" for two attributes "A" and "B" is determined to be 64 and 16, respectively.

To identify attribute "A," two pools are prepared: pool D64-1 (element 1780) comprises samples 1-64, and D64-2 (element 1781) comprises samples 65-128. Note that for "A," the source tag sharing number "d" is equal to "Max PoolSz," therefore source tagging is optional for these two pools.

To identify attribute "B," 8 pools (element 1782) are prepared, each comprising 16 biological samples sharing a source tag. Thus, pool D16-1 comprises samples 1-16, D16-2 comprises samples 17-32 . . . D16-8 comprises samples 113-28. Source tags are added to each pool. Then, two pooled pools (elements 1783 and 1784) are prepared. A first pooled pool 1783 comprises pools D16-1 through D16-4, containing biological samples 1-64, for a total of 64 total biological samples (="Max PoolSz"). Similarly, a second pooled pool 1784 comprises pools D16-4 through D16-8, containing biological samples 65-128, for a total of 64 total biological samples (="Max PoolSz").

Attribute specific marker tag for attribute "A" is added to each of pools 1780 and 1781. Interrogation of the produced reaction products in pools 1780 and 1781 reveals no signal for attribute "A" in pool 1780 (unambiguous result) and a signal for attribute "A" in pool 1781 (ambiguous result). This result indicates that at least one of the 64 biological samples, consisting of biological samples 65-128, in pool 1781 expresses attribute "A." To disambiguate these data, the attribute-specific probe for "A" can be added to pooled pool 1784, concurrent with the addition of the attribute-specific marker tag for attribute "B." Interrogation of the produced reaction products will indicate which of the pools D16-5 to D16-8 contains the biological sample expressing attribute "A," while also identifying whether attribute "B" is present in any of the pools. As discussed above, these steps may be repeated until the source tag sharing number "d" is reduced to 1, in which case there will be no ambiguities because biological samples do not share a source tag with a source tag sharing number "d"=1.

Figure 18:
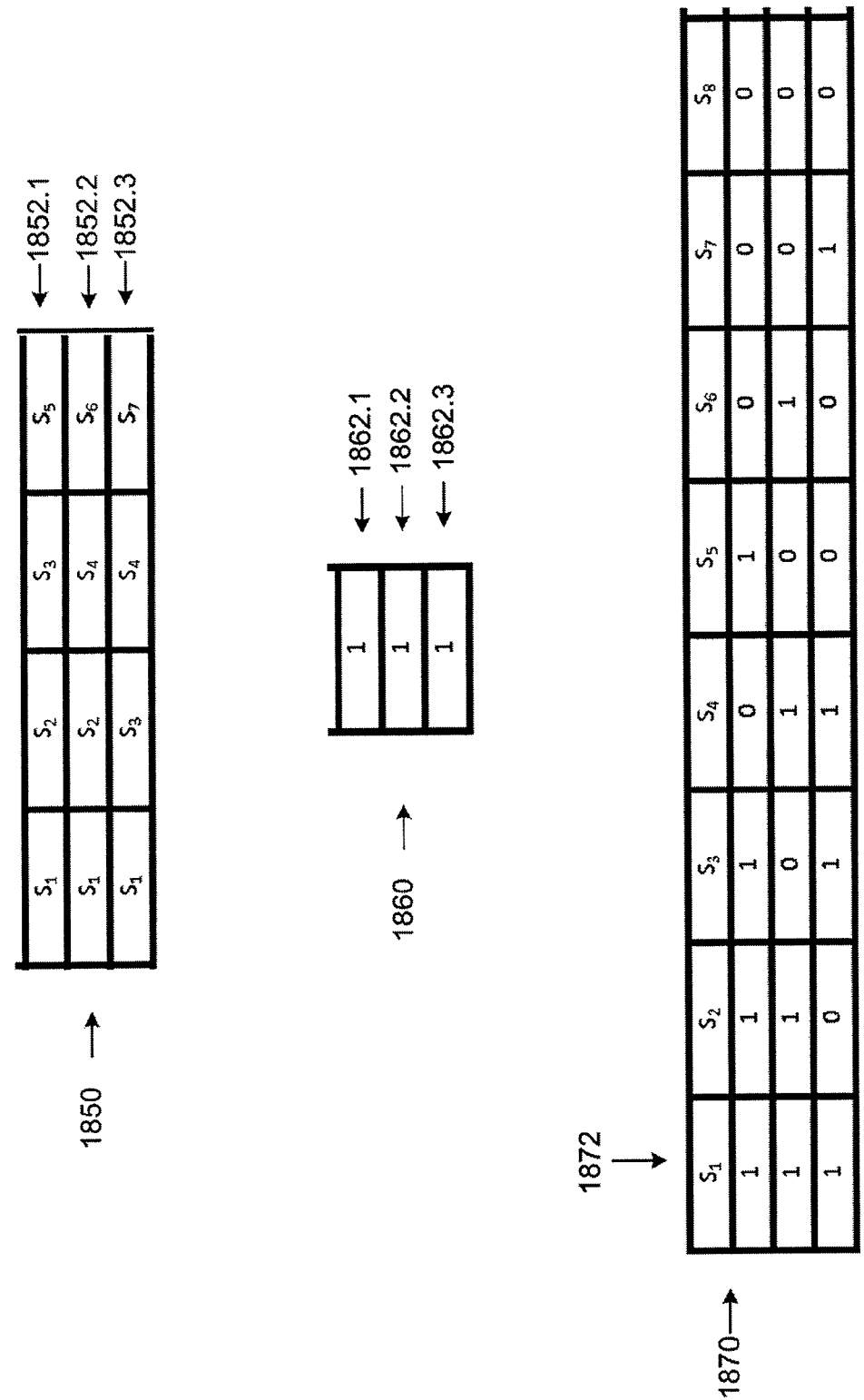
FIG. 18 schematically illustrates binary deconvolution for the case where "d"=8, when there is an ambiguity for an antigen group with two antigens.

In some embodiments, a method of deconvolution may be used to disambiguate ambiguities arising from performing the method 50 of FIG. 3. Illustrated in FIG. 18 is an example of a method of deconvolution for the case with the source tag sharing number "d"=8, when there is an ambiguity in determining a polymorphism having two alleles. For example, the polymorphic site may be K(½) from table 1720 (of FIG. 17A) and the results in step (d) of method 50 may have indicated that at least one of the samples sharing a source tag contained the variant form of the allele at the polymorphic site (with a percentage frequency of 0.01 or 1%).

To disambiguate the results, three different operations are performed with different subsets of four of the eight samples sharing the same source tag, as illustrated in table 1850. The first operation 1852.1 in FIG. 18 pools $sample_1$, $sample_2$, $sample_3$, and $sample_5$, and then reacts the pool with an attribute-specific marker tag for the variant antigen of K(½) to determine whether or not any of the samples contain the variant antigen. The result is scored as either 0 or 1, and may be recorded in the table 1860. It is assumed for purposes of this example the result is 1 and is recorded at 1862.1 of FIG. 18. Similarly, the second operation 1852.2 pools $sample_1$, $sample_2$, $sample_4$, and $sample_6$, and then reacts the pool with an attribute-specific marker tag for the variant antigen of K(½) to determine whether or not any of the samples contain the variant antigen. It is assumed for purposes of this example that the result is 1 and is recorded at 1862.2 of FIG. 18. Similarly, the third operation 1852.3 pools $sample_1$, $sample_3$, $sample_4$, and $sample_7$, and then reacts the pool with an attribute-specific marker tag for the variant antigen of K(½) to determine whether or not any of the samples contain the variant antigen. It is assumed for purposes of this example that the result is 1 and is recorded at 1862.3 of FIG. 18.

The sample that is positive for the variant allele K(½) can then be identified by examining table 1870 of FIG. 18. Table 1870 identifies which of the samples contains the variant antigen based on the results of the three operations performed above. Here, table 1860, with the single column of three 1's matches column 1872 of table 1870, which also has three 1's. Thus, $sample_1$ is the identified sample containing the variant antigen K(½). $Sample_1$ is the sample that contains the variant antigen because $sample_1$ is the only sample that was included in all three operations performed above and all three operations indicated the presence of the variant allele. However, it can not be conclusively determined that $sample_1$ contains the variant allele, because more than one sample may contain the variant antigen. In some embodiments, an additional operation may be perform on seven of the eight samples excluding $sample_1$. If the result of the operation on the seven samples indicates that none of the seven samples contains the variant antigen, then the ambiguity has then been resolved, and it is certain that $sample_1$, and only $sample_1$, of the eight samples contains the variant antigen.

Identifying Antigens where "d" is Equal to "Max PoolSz"

Maximum pool size "Max PoolSz" refers to the maximum number of biological samples that may be pooled together. As discussed previously, the value of "Max PoolSz" may be determined by limitations arising from steps of the method. In some embodiments, the source tag sharing number "d" determined for an attribute is equal to or greater than "Max PoolSz." In these embodiments, the biological samples to be pooled for each attribute for which the "d" is equal or greater than the "Max PoolSz" do not require a source tag. As described previously and illustrated in FIG. 17A, if the source tag sharing number "d" determined for an attribute is greater than "Max PoolSz," then "Max PoolSz" may be used as the source tag sharing number "d" for that attribute. Thus, the source tag sharing number "d" may be a value described by $1 \leq "d" \leq "Max\_PoolSz."$ In this embodiment, steps 110(*a*) and 120(*b*) of method 50 in FIG. 3 are carried out as previously discussed. Step (c) in this embodiment comprises the following: for each pool of the plurality of pools for the source tag sharing number "d," produce at least one pooled pool comprising attribute-specific reaction products: (i) for each pool of the plurality of pools for the source tag sharing number "d" where the source tag sharing number "d" is less than a maximum_pool_size, producing at least one pooled pool comprising attribute-specific source-tagged reaction products from at least two pools of the plurality of pools for each of the different determined source tag sharing numbers "d," wherein the attribute-specific reaction products comprise attribute-specific source-tagged reaction products comprising a source tag identifying said each pool and a marker tag that uniquely identifies an attribute; and (ii) for each pool of the plurality of pools for the source tag sharing number "d," where the source tag sharing number "d" is equal to the maximum_pool_size, producing at least one reaction pool comprising attribute-specific reaction products from each pool of the plurality of pools, wherein the attribute-specific reaction products comprise a marker tag that uniquely identifies an attribute, and wherein each said reaction pool is the at least one pooled pool.

Thus, for the attributes wherein the source tag sharing number "d" is equal to the maximum_pool_size, it is not necessary to produce a pooled pool of attribute-specific source-tagged reaction products. Instead, the pooled pool is a reaction pool comprising attribute-specific reaction products. The attribute-specific reaction products result from contacting a pool containing "Max PoolSz" biological samples with a marker tag for each attribute having a source tag sharing number "d" equal to the maximum_pool_size.

Method 50 in this embodiment continues with Step 220 (*d*), which comprises: identifying said reaction products comprising attribute-specific source-tagged reaction products or attribute-specific reaction products by interrogating said reaction products, and if the interrogating of said reaction products indicates unambiguous results, then identifying said attributes, otherwise if the interrogating of said reaction products indicates ambiguous results, then disambiguating the ambiguous results, thereby identifying attributes of the plurality of biological samples.

Other Embodiments and Variations

In an embodiment, method 50 of FIG. 3 further includes a step directed to screening pools (e.g., pools comprising up to "Max PoolSz" number of biological samples) in order to identify those pools which may have ambiguities. This embodiment involves detection of antibody-mediated agglutination using methods known in the art. "Agglutination" refers to clumping or aggregating of particles, such as cells, in the presence of an antibody. "Hemagglutination" refers to the agglutination of red blood cells. "Leukoagglutination" refers to the agglutination of white blood cells. Cells to which antibodies are bound can be agglutinated by the addition of an agglutination agent, such as IgM. The resulting complex prevents or substantially retards the migration of the complex, for instance, through a gel matrix under a controlled spin. In another embodiment, detection of agglutination uses antibody-functionalized magnetic particles as the agglutination agent, which, when mediating agglutination, permit the retention of agglutinated cells in a magnetic field. Agglutination can also be detected in solution, as discussed below.

Accordingly, steps 110 (*a*) and 120 (*b*) of method 50 are carried out to produce a plurality of pools for the source tag sharing number "d," wherein each pool comprises a pooled subset of biological samples. An unlabeled antibody specific to an attribute having source tag sharing number "d" is added to the pool and agglutination is assessed. Unlabeled antibodies specific to the attributes having the same source tag sharing number "d," are added to the pool and agglutination is assessed. Detection of agglutination in a pool (e.g., "a positive pool"), for instance by visual inspection, indicates that at least one biological sample in the pool comprises the attribute. Such positive pools are thus preliminarily identified as having an ambiguity. Agglutination can be assessed for biological samples comprising source tags, provided the source tag does not comprise an antibody.

A plurality of attributes may be tested as well. In this embodiment, a plurality of unlabeled antibodies specific to the plurality of attributes is added to the pool and agglutination is tested. Detection of a positive pool indicates that at least one biological sample in the pool comprises at least one of the plurality of attributes. In some embodiments, the antibodies specific to the attributes further comprise a detectable label, such as a fluorescent color, such that each attribute-specific antibody has a different label. Positive pools may then be interrogated by detecting the fluorescent color in the agglutinated cells to identify which attribute is present. In another embodiment, positive pools may be interrogated by the use of anti-tags to identify which attribute is present.

Positive pools can be disambiguated as discussed above. Specifically, for positive pools, method 50 of FIG. 3 is carried out with the source tag sharing number "d" reduced, so that the number of biological samples in pools sharing a source tag is reduced. For example, if the agglutination screening step is performed with the source tag sharing number "d"=64, and an ambiguity is detected at an antigen for the 64 biological samples pooled together, then the method may be performed with the 64 biological samples with a source tag sharing number less than 64, for example d="16."

Numerous commercial products exist for assessing agglutination. See, for instance, MDmulticard® (Grifols S. A., Barcelona, Spain) and ID-Antigen Profile products (Bio-Rad Laboratories).

In an embodiment, agglutination is detected in solution using a capillary flow device, schematically illustrated in FIGS. 19A and 19B. Cells such as blood cells have been separated in such capillary flow devices. See, Davis et al. 2006, PNAS 103:14779-14784; Radisic et al., 2006, Int J Nanomedicine 1:3-14). The device 1900 comprises a substrate 1905 comprising a planar array of posts 1910, or pillars, typically 50-100 micrometer in height ("H", FIG. 19A), within a rectangular (or square) channel 1920, typically several mm in width ("W") and length ("L") (FIG. 19B), and having an adjacent inlet 1925. Such devices preferably are fabricated by way of standard methods of semiconductor "micromachining." An exemplary illustration is on p. 26 of Sritharan (2009, "Size-based cell sorting by deterministic lateral displacement" (2009). *Chemical Engineering Master's Theses.* Paper 8; http://hdl.handle.net/2047/d10019078). The device 1900 is bonded to a planar glass cover 1930 (by standard methods such as anodic bonding), to form a "sandwich" cell permitting optical observation of the flow channel, thus forming a leak-tight assembly in a "sandwich" configuration. Exemplary bonding methods are known in the art. See, for instance, Gale (2001, "Bonding, Packaging and Sacrificial Processes" http://www.eng.utah.edu/~gale/mems/Lecture%2016a%20Bonding.pdf). Alternative methods that enable the fabrication of such devices in "soft" materials, such as polydimethylsiloxane, are also known in the art. See, for instance, Zhao et al. (2006, Sensors and Actuators A 125 (2006) 398-404). Disposable devices of this type thus may be fabricated at scale in order to reduce unit cost.

In a particularly preferred embodiment, the center-to-center distance of the posts decreases with distance from the inlet, along the length "L", and optionally also along the width "W" of the channel, as illustrated in FIG. 19B. The resulting increase in lateral post density increases the available post surface area, and, if post surfaces are hydrophilic, the device provides for controlled differential evaporation of aqueous solutions. Post surfaces can be made hydrophilic by methods known in the arty, such as silicon oxidation. Thus, an aliquot of solution, placed into the inlet of a dry device will, by way of capillary action, fill the available channel volume, typically $V=L*W*H$ (e.g., 10 mm*5 mm*0.1 mm=5 ul). As the liquid evaporates, the gradient in available hydrophilic post surface area will concentrate the remaining fluid in the region of highest post density, that is, to the right end of the channels in FIG. 19B. Cells suspended in solution will travel from left to right, along the channel, at a rate of migration that may be determined by controlling the rate of evaporation. By leaving sufficient clearance between posts for individual red blood cells 1940, but not agglutinated cells 1950 to pass through the array, agglutinated cells are readily separated from non-agglutinated cell.

In contrast to a widely used commercial method of column chromatography for the detection of agglutination which comprises a gel matrix incorporating antibodies (such as ID MicroTyping System™, Ortho Clinical Diagnostics), the post-array capillary flow device detects agglutination, mediated by antibodies ("direct" agglutination) or secondary antibodies ("indirect" agglutination/Coombs test) in solution.

The method of the invention can also be practiced to identify the presence or absence of a cell surface marker on a cell. In this embodiment, a reference level for cell surface expression of the target attribute in the biological sample must be known or established for a marker tag, e.g., a fluorescent color, to be used. Ascertaining a reference level for the expression of a cell surface marker is conventional in the art. Given the reference level, one can calculate the fluorescence expected for the number of biological samples present. If the detected fluorescence level is the same as the expected fluorescence level or within a statistically significant range of levels, for instance within one standard deviation, then it may be concluded that all of the biological samples in the pool express the cell surface marker. If the detected fluorescence level is less than the expected fluorescence level to a statistically significant degree, such as outside one standard deviation, it may be concluded that expression of the cell surface at least one biological sample present in the pool does not comprise the cell surface marker. This result may be an ambiguous result if there are two or more biological samples having the same source tag. In that case, the results must be disambiguated. By such means, the cell surface marker profile can be identified for a plurality of biological samples.

In some embodiments, the method can be used to profile a set of attributes in which altered expression is associated with a particular medical condition. As used herein, a "medical condition" refers to any disease or disorder or injury that might affect a subject's health, benefit from medical assistance, or have implications for medical treatments. The term also includes normal health conditions, such as pregnancy, The expression levels for a set of antigens associated with a medical condition is often referred to as a "signature." The altered expression can be either an increase in antigen cell surface expression or a decrease in antigen cell surface expression. In this embodiment, the cell surface expression levels of a plurality of antigens is identified. For each antigen, a threshold level of expression is established such that expression that exceeds the threshold level is designated as altered. For instance, for an antigen in which elevated expression is associated with the particular medical condition, detecting a level above that threshold expression level is designated elevated expression, and expression at or below the threshold level is designated as not elevated. For an antigen in which reduced expression is associated with the particular medical condition, detecting a level below the threshold expression level is designated as reduced expression, and expression at or above the threshold level is designated as not reduced.

Establishing a threshold to distinguish between two possibilities, such as normal expression and altered expression, is well known to skilled artisan. Receiver operating characteristic (ROC) curve analysis is commonly used in this regard. See, for instance, Fawcett (2006) Pattern Recognition Letters 27:861-874); Pasanen et al. (1993, Br J. Cancer. 67(4): 852-855); and Greiner et al. (2000) Prev Vet Med. 30:23-41. Establishing a threshold is conventional in the development of diagnostic assays. For instance, as the skilled artisan is aware, the accuracy of a diagnostic test is commonly measured by its sensitivity and specificity. The skilled artisan is well aware that distributions of data from healthy and diseased persons almost always overlap (see, for instance, page 6 of Sacher et al., *Widmann's Clinical Interpretation of Laboratory Tests*, "Principles of Interpretation of Laboratory Tests", $11^{th}$ edition, F. A. Davis Company, Philadelphia, Pa., 2000, pp. 3-27). As discussed in Sacher et al., the region of overlap concerns "false positives" in the healthy group and "false negatives" in the diseased group. Sensitivity and specificity, which are calculated based on a threshold value separating values identified as "healthy" and values identified as "diseased" (Ibid, pp. 5-6, FIG. 1-1 and text), describe the frequency of such false negatives and false positives, respectively, for a diagnostic dataset. While the ideal diagnostic test would have both specificity and sensitivity of 100%, that is, a test with no false positives and no false negatives, this high standard cannot generally be met (Ibid, p. 6, final paragraph). That is, the typical diagnostic test is for a likely diagnosis, not a definitive diagnosis. In some embodiments, the threshold level is a threshold value as discussed in Sacher et al. (ibid). In some embodiments herein, the threshold is a threshold value selected for a high specificity. In other embodiments, the threshold level is a threshold value selected for a high sensitivity.

In some embodiments of the method, where the source tag sharing number "d" determined for at least one attribute is equal to "Max PoolSz," the method comprises identifying at least two attributes wherein there is at least one attribute for which the source tag sharing number "d" is determined to be less than "Max_PoolSz."

In some embodiments of the method, the method comprises identifying at least two attributes, wherein the source tag sharing number "d" for a first attribute is different from the source tag sharing number "d" for the at least second attribute. In an embodiment, the source tag sharing number "d" is determined based on the frequency of the attribute. In another embodiment, the source tag sharing number "d" is determined based on the level of expression of the attribute.

In another embodiment, the method of the invention can be used to determine an allele profile of a nucleic acid. This embodiment is described in commonly-assigned, co-pending application entitled "METHOD FOR DETERMINING AN ALLELE PROFILE OF NUCLEIC ACID," filed on even date herewith, which is incorporated herein by reference in its entirety.

The disclosures of each and every patent, patent application, and publication cited herein are hereby incorporated herein by reference in their entirety.

While the methods have been disclosed with reference to specific embodiments, it is apparent that other embodiments and variations may be devised by others skilled in the art without departing from the true spirit and scope of the described method. The appended claims are intended to be construed to include all such embodiments and equivalent variations.

What is claimed is:

1. A method of identifying attributes for at least two biological samples in a plurality of biological samples, the method comprising:
   (a) binning one or more of the attributes to be identified based on the attributes to be binned having the same source tag sharing number "d",
   wherein said source tag sharing number "d" is determined based on a frequency of the one or more attributes to be identified,
   wherein if said number "d" is not an integer, then said number "d" is set to the closest positive integer that is less than "d";
   provided that if "d" is less one, then "d" is set to one;
   further provided that if the resulting integer "d" exceeds a preset upper limit of "d", it is replaced by said preset upper limit of "d", wherein said preset upper limit of "d" is the lesser of:
   (i) a value of "d" determined by the condition that the probability of an ambiguity in the identification of said attributes occurring in "d" biological samples of the plurality of biological samples does not exceed a user-selected highest acceptable probability of an ambiguity in the identification of said attributes occurring in "d" biological samples of the plurality of biological samples;
   provided that the user-selected highest acceptable probability of an ambiguity is not 0 or 1 and provided that the frequency of a variant attribute based on the attributes to be identified is not 0; and
   (ii) the maximum pool size, which is a number of biological samples that may be pooled, wherein the number is greater than one and is based on technical limitations of performing the steps of the herein method of identifying attributes;
   (b) collecting aliquots from the plurality of biological samples and combining "d" number of said aliquots to form at least one biological sample pool;
   (c) (i) performing a reaction in each biological sample pool to produce reaction products comprising a source tag identifying each said pool, wherein said reaction is performed using as templates said biological samples in each said pool;
   (ii) if "d" is less than the maximum pool size, then forming at least one pooled pool comprising at least some of the said produced reaction products from a number of pools, said number determined as a result of dividing the maximum pool size by "d";
   (iii) if "d" is equal to the maximum pool size, then proceeding to step (d) without forming pooled pools;
   (d) for each of the attributes to be identified, performing a second reaction in the at least one pool or pooled pool using said reaction products comprising said source tag to produce attribute-specific second reaction products comprising a marker tag and a derived source tag, wherein said derived source tag is at least one of: said source tag, a copy of said source tag, or a copy of the complement of the source tag, and wherein said marker tag identifies an attribute;
   (e) interrogating said marker tags;
   (f)(i) if all marker tags in a pool or pooled pool are identical and correspond to an attribute of the one or more attributes to be identified, then identifying the biological samples in said pool or pooled pool as being homozygous for said attribute of the one or more attributes to be identified;
   (ii) if all marker tags in a pool or pooled pool are not identical, then interrogating the derived source tags of the second reaction products in said pool or pooled pool to determine which biological samples were placed into that pool or pooled pool and identifying the marker tags of the second reaction products in said pool or pooled pool to determine if said pool or pooled pool comprises a second reaction product with at least one marker tag corresponding to an attribute of the one or more attributes to be identified, and, if so, identifying the biological samples in said pool or pooled pool as containing at least one copy of an attribute of the one or more attributes to be identified; and
   (g) for the biological samples identified in (f)(ii), repeating steps (a)-(f) as needed with said identified biological samples until all of the attributes for the biological samples have been identified, wherein in carrying out repetitions of steps (a)-(f) "d" is replaced by an integer "d*" that is different than "d".

2. The method of identifying attributes of claim 1, wherein step (f)(ii) further comprises:
   performing a method of deconvolution for each attribute that was not identified because the interrogating of said second reaction products indicates ambiguous results.

3. The method of identifying attributes of claim 1, wherein said marker tag of said reaction products comprises at least one of the following to identify an attribute: an oligonucleotide tag or a fluorescent tag.

4. The method of identifying attributes of claim 3, wherein each of said attributes is an antigen of a blood group and attributes of a plurality of blood groups are identified.

5. The method of identifying attributes of claim 4, wherein said marker tag comprises an oligonucleotide tag comprising a first nucleotide sequence to identify an attribute and a second nucleotide sequence to identify a blood group.

6. The method of identifying attributes of claim 4, wherein said marker tag comprises an oligonucleotide tag that comprises a nucleotide sequence to identify both a blood group system of the plurality of blood groups and said antigen.

7. The method of identifying attributes of claim 4, wherein said marker tag of said reaction products comprises at least one of the following to identify a blood group system of the plurality of blood groups: an oligonucleotide tag or a fluorescent tag.

8. The method of identifying attributes of claim 1, wherein in step (e) interrogating comprises:
   interrogating said derived source tag and said marker tag of said second reaction products by contacting said second reaction products with microparticles, said microparticles comprising a first capture probe capable of capturing said source tag and comprising an optical tag that identifies said microparticle.

9. The method of identifying attributes of claim 8, wherein said microparticles further comprise a second capture probe capable of capturing said marker tag.

10. The method of identifying attributes of claim 9, wherein said marker tag is an oligonucleotide tag and said second capture probe is complementary to said marker tag.

11. The method of identifying attributes of claim 10, wherein interrogating said marker tags comprises:
    interrogating said marker tag of said second reaction products by contacting said reaction products with anti-tags of said marker tags; and identifying anti-tags that anneal to said marker tags.

12. The method of identifying attributes of claim 11, wherein the interrogating comprises determining a length of the anti-tags by electrophoretic separation of said anti-tags.

13. The method of identifying attributes of claim 11, wherein said anti-tags comprise an optical tag.

14. The method of identifying attributes of claim 10, wherein said marker tag comprises an unique nucleotide sequence.

15. The method of identifying attributes of claim 8, wherein said marker tag comprises an optical tag.

16. The method of identifying attributes of claim 15, wherein said optical tag is a fluorescent tag.

17. The method of identifying attributes of claim 8, wherein said source tag is an oligonucleotide tag and said first capture probe is complementary to said source tag.

18. The method of identifying attributes of claim 17, wherein said source tag comprises an unique nucleotide sequence.

19. The method of identifying attributes of claim 1, wherein each of said attributes is an antigen of a blood group and attributes of a plurality of blood groups are identified and wherein said marker tag uniquely identifies an antigen of a blood group.

20. The method of identifying attributes of claim 1, wherein said attributes are expression levels of antigens in a collection of antigens, wherein altered expression levels of said antigens in said collection of antigens is associated with a medical condition.

21. The method of identifying attributes of claim 1, wherein said attributes are the presence or absence of antigens in a collection of antigens.

22. The method of identifying attributes of claim 1, wherein said attributes are antigens.

23. The method of identifying attributes of claim 22, further comprising prior to step (c),
    adding to each pool an antibody specific to at least one attribute in each pool;
    contacting each pool with an agglutination agent; and
    assessing agglutination for each pool,
wherein detecting the presence of agglutination indicates at least one biological sample of the pooled subset of biological samples comprises said at least one attribute.

24. The method of claim 1 wherein said source tag sharing number "d" is determined using the following formula: $d=0.5*\log(1-C)/\log(1-f(V))$;
    wherein C is said user-selected highest acceptable probability of an ambiguity and f(V) is the frequency of a variant attribute.

25. The method of claim 1 wherein if the value of "d" is not a natural number of the form $2^n$, wherein n is a non-negative integer, then "d" is set to the nearest natural number of the form $2^n$ that is less than "d".

26. The method of claim 1 wherein the value of "d" is set to the closest integer less than or equal to the maximum pool size.

27. The method of claim 1 further comprising repeating steps (a)-(g) as needed with one or more additional attributes as the one or more desired attributes.

* * * * *